US005599922A

United States Patent [19]
Gryaznov et al.

[11] Patent Number: 5,599,922
[45] Date of Patent: Feb. 4, 1997

[54] OLIGONUCLEOTIDE N3'-P5' PHOSPHORAMIDATES: HYBRIDIZATION AND NUCLEASE RESISTANCE PROPERTIES

[75] Inventors: Sergei M. Gryaznov, San Mateo; Ronald G. Schultz, Fremont; Jer-kang Chen, Palo Alto, all of Calif.

[73] Assignee: Lynx Therapeutics, Inc., Hayward, Calif.

[21] Appl. No.: 214,599

[22] Filed: Mar. 18, 1994

[51] Int. Cl.⁶ ............................. C07H 21/04; C12Q 1/68
[52] U.S. Cl. ........................... 536/25.3; 536/23.1; 435/6
[58] Field of Search ................................ 536/23.1, 25.3; 435/6

[56] References Cited

U.S. PATENT DOCUMENTS 5,271,941  12/1993  Cho-Chung ............................ 424/450
5,476,925  12/1995  Letsinger et al. ...................... 536/23.1

FOREIGN PATENT DOCUMENTS

0490281A1  12/1991  European Pat. Off. .
0552766A2   1/1993  European Pat. Off. .
4129318A1   3/1993  Germany .

OTHER PUBLICATIONS

Mag et al. (1992) "Synthesis and Selective Cleavage of an Oligodeoxynucleotide Containing a Bridged Non–Chiral Internucleotide 3'–Phosphoramidate . . . " Tetrahedron Letters 33: 7319–7322.
Milligan et al. (1993) "Current Concepts in Antisense Drug Design" J. Med. Chem. 36: 1923–1937.
Uhlmann et al (1990) "Antisense Oligonucleotides: A New Therapeutic Principle" Chemical Rev. 90: 543–584.
Dagle et al. (1991)"Physical Properties of Oligonucleotides Containing Phosphoramidates–Modified Internucleotide Linhages". Nucleic Acids Res. 19: 1805–1810.
Gryaznov, et al. Synthesis and Properties of Oligonucleotides Containing Aminodeoxythymidine Units, (1992), Department of Chemistry, Northwestern University, (Nucleic Acids Research) vol. 20, No. 13, pp. 3403–3409.
Ratajczak, et al. In Vivo Treatment of Human Leukemia in a Scid Mouse Model with C–myb Antisense Oligodeoxynucleotides, (1992), Proc. Natl. Acad. Sci, USA, vol. 89, pp. 11823–11827.
Szczylik, et al., Selective Inhibition of Leukemia Cell Proliferation by BCR–ABL Antisense Oligonucleotides, (1991), *Science*, vol. 253, pp. 562–565.
Zielinski, et al., Autocatalytic Synthesis of a Tetranucleotide Analog, (1987) *Nature* (London), 327 (6120), 346–7 (Abstract).

*Primary Examiner*—George C. Elliott
*Assistant Examiner*—Scott D. Priebe

[57] ABSTRACT

Modified oligonucleotide 3'-NHP(O)(O⁻)O-5' phosphoramidates were synthesized on a solid phase support. The phosphoramidate analogs were found to have significantly increased resistance toward phosphodiesterase digestion. Thermal dissociation experiments demonstrated that these compounds form more stable duplexes than phosphodiesters with complementary DNA and particularly RNA strands. Further, the phosphoramidate analogs can also form stable triplexes with double-stranded DNA target, where under similar conditions parent phosphodiester compounds failed to do so.

32 Claims, 17 Drawing Sheets

Fig. 3

| Expt. | Oligonucleotide Sequences | No. | Target | $T_m$ (°C)[A] |
|---|---|---|---|---|
| 1 | TTTTTTTTT; 1 | 1 | poly dA | 29.7 |
| 2 | same as experiment 1 | 1 | poly A | 27.0 |
| 3 | TnpTTnpTTnpTTnpTnpt; 2 | 2 | poly dA | 25.8 |
| 4 | same as experiment 3 | 2 | poly A | 33.7 |
| 5 | TnpTnpTnpTnpTnpTnpTnpTnpT; 3 | 3 | poly dA | 36.0 |
| 6 | same as experiment 5 | 3 | poly A | 51.5 |
| 7 | same as experiment 5 | 3 | 5'dAAAAAAAAA C4<br>5'TTTTTTTTT | 32.0;<br>47.2[B] |
| 8 | d CTTCTTCCTTA; 4 | 4 | dATAAGGAAGAAGC | 37.5 |
| 9 | same as experiment 8 | 4 | rAUAAGGAAGAAGC | 49.5 |
| 10 | same as experiment 8 | 4 | rAUAAGGUAGAAGC[C] | 35.1 |
| 11 | rCTTCTTCCTTA; 5 | 5 | rAUAAGGAAGAAGC | 54.4 |
| 12 | same as experiment 11 | 5 | rAUAAGGUAGAAGC | 42.0 |
| 13 | dCnpTnpTnpCnpTnpTnpCnpTnpTnpA; 6 | 6 | dATAAGGAAGAAGC | 49.2 |
| 14 | same as experiment 13 | 6 | rAUAAGGAAGAAGC | 72.4 |
| 15 | same as experiment 13 | 6 | rAUAAGGUAGAAGC | 60.2 |
| 16 | same as experiment 13 | 6 | 5'dTTCCTTCTTTC T4<br>3'AAGGAAGAAAG | 57.0;<br>62.0[B] |

| Expt. | Oligonucleotide | Tm |
|---|---|---|
| 1 | TATATATATA<br>          T4;<br>ATATATATAT | 37.0 |
| 2 | TnpATnpATnpATnpA<br>                T4;<br>A  TA  TA  TA  T | 42.0 |
| 3 | TnpATnpATnpATnpA<br>                T4;<br>ApnTApnTApnTApnT | 61.5 |
| 4 | TACGTACGTA<br>          T4;<br>ATGCATGCAT | 59.5 |
| 5 | TnpACnpGTnpACnpGTnpA<br>                    T4;<br>A  T  G  CA  TG   CA T | 62.2 |
| 6 | TnpACnpGTnpACnpGTnpA<br>                    T4;<br>ApnTGpnCApnTGpnCApnT | 67.0 |

Fig. 6

OLIGONUCLEOTIDE N3'-P5' PHOSPHORAMIDATES: HYBRIDIZATION AND NUCLEASE RESISTANCE PROPERTIES

FIELD OF THE INVENTION

The present invention relates to hybridization and nuclease resistance methods employing oligonucleotide N3'→P5' phosphoramidates.

REFERENCES

Abergo, D. D., et al., *Biochemistry* 20:1409–1413 (198).

Agrawal, S., et al., *Proc. Natl. Acad. Sci. USA* 86.:7790–7794 (1989).

Anfossi, G., et al., *Proc. Natl. Acad. Sci. USA* 86:3379 (1989).

Atherton, R. F., et al., *J. Chem. Soc., pp.* 660–663 (1945).

Ausubel, F. M., et al., *Current Protocols in Molecular Biology*, John Wiley and Sons, Inc., Media Pa.

Azhayez, A. V., et al., *Bio Organ. Khimiya* 8(9):1218–1224 (1982).

Baer, M. R., et al., *Blood* 79(5):1319–1326 (1992).

Bannwarth, W., *Helv. Chem. Acta* 71:1517–1527 (1988).

Bayever, E., et al., *Antisense Research and Development* 3:383–390 (1993).

Birg, F., et al., *Nucleic Acids Research* 18 (10), 2901–2908 (1990).

Borer, P. N., in *Handbook of Biochemistry and Molecular Biology*, Vol. 1, 3rd Ed., CRC Press, Cleveland, Ohio, pp. 589 (1975).

Bower, M., et al., *Nucl. Acids Res.* 15:4915–4930 (1987).

Calabretta, B., et al., *Seminars in Cancer Biol.* 3 (6):391–398 (1992).

Calabretta, B., et al., *Cancer Treatment Rev.* 19(2):169–179 (1993).

Cogswell, P. C., et al., *J. Immunol.* 150(7):2794–804 (1993).

Cohen, J. S., in *Antisense Research and Applications* (Crooke, T. S., et al., Eds.) CRC Press, Boca Raton, Fla., pp. 205–221 (1993).

Collins, S. J., et al., *Nature* 270:347–349 (1977).

Collins, S. J., et al., *Science* 225:72 (1984).

Cook, K. S., et al., *Nucleic Acids Res.* 19: 1577–1583 (199).

Cooney, M., et al., *Science* 241:456–459 (1988).

Cordingley, M. G., et al., *Proc. Natl. Acad. Sci.* USA 87: 8985–8989 (1990).

Cowsert, L. M., et al., *Antimicrob. Agents and Chemo.* 37 (2):171–177 (1993).

Cutry, A. F., et al., *J. Biol. Chem.* 264(33):19700–119705 (1989).

Daley, G. Q., et al., *Proc. Natl. Acad. Sci. USA* 85:9312–9316 (1988).

Dayton, A. I., et al., *Cell* 44:941–947 (1986).

Dingwall, C., et al., *Proc. Natl. Acad. Sci. USA* 86: 6925–6929 (1989).

Donia, B. P., et al., *J. Biol. Chem.* 268 (19):14514–14522 (1993).

Eckstein, F., *Ann. Rev. Biochem.* 54:367–402 (1985).

Fisher, A. G. et al., *Nature* 320:367–371 (1986).

Froehler, B., et al., *Nucl. Acids Res.* 16.:4831–4839 (1988).

Gale, R. P., et al., *Proc. Natl. Acad. Sci. USA* 81:5648 (1984).

Glinski, R. P., et al., *Chemical Comm.*, pp. 915–916 (1970).

Goldberg, M. L. et al., *Methods in Enzymology* 68:206 (1979).

Goodchild, J., *Bioconjugate Chem.* 165–187 (1990).

Grigoriev, M., et al., *Proc. Natl. Acad. Sci. USA* 90(8):3501–3505 (1993).

Gryaznov, S. M., et al., *Vest. Mosk. Univ. Ser.* 2: *Khim* 27:421–424 (1986).

Gryaznov, S. M., et al., *Tetrahedron Lett.* 31:3205–3208 (1990).

Gryaznov, S. M., et al., *Nucl. Acids Res.* 20:3403–3409 (1992).

Helene, C., et al., *Biochem. Biophys. Acta* 1049:99–125 (1990).

Helene, C., and J.-J. Toulme, *Biochimica et Biophysica Acta* 1049, 99–125 (1990).

Helene, C., *Anti-Cancer Drug Design* 6:569–584 (1991).

Herdewijn, P., and van Aerschot, A., *Tetrahedron Lett.* 30:855 (19891).

Higgins, K., et al., *Proc. Natl. Acad. Sci. USA* 90:9901–9905 (1993).

Holland, S. M., et al., *J. Virol.* 64:5966–5975 (1990).

Kawasaki, A. M., et al., *J. Medicinal Chem.* 6(7):831–841 (1993).

Kibler-Herzog, L., et al., *Nucl. Acids. Res.* 19:2979–2986 (1991).

Kjems, J., et al., *Proc. Natl. Acad. Sci. USA* 88:683–687 (1991).

Kulka, M., et al., *Antiviral Res.* 20(2):115–130 (1993).

LaPlauche, L. A., et al., *Nucl. Acids Res.* 14:9081–9093 (1986).

Letsinger, R. L., et al., *J. Am. Chem. Soc.* 110:4470–4471 (1988).

Letsinger, R. L., U.S. Pat. No. 4,958,013, issued on 18 Sep. 1990.

Li, G., et al., *J. Virol.* 67(1):6882–6888 (1993).

Lui, M. W., et al., *Circulation* 79: 1374–1387 (19891).

Mag, M., et al., *Tetrahedron Lett.* 33:7319–7322 (1992).

Malim, M. H., et al., *Nature* 338:254–257 (1989*a*).

Malim, M. H., et al., *Cell* 58:205–214 (1989*b*).

Maniatis, T., et al. *Molecular Cloning: A Laboratory Manual*, Cold Spring Harbor Laboratory (1982).

Marky, L. A., et al., *Biopolymers* 26:1601–1620 (1987).

Marshall, W. S., et al., *Science* 259:1564 (1993).

Matsukura, M., et al., *Proc. Natl. Acad. Sci. USA* 86:4244–4248 (19891).

McShan, W. M., et al., *J. Biological Chem.* 267 (8):5712–5721 (1992).

Miller, P. S., *Bioconjugate Chem.* 1:187–191 (1990).

Miller, P. S., *Biotechnology* 9:358–361 (1991).

Mitunobu, O., *Synthesis* 1–28 (1981).

Muesing, M. A., et al., *Cell* 48:691–701 (1987).

Mullis, K. B., et al., U.S. Pat. No. 4,683,195, issued 28 Jul. 1987.

Mullis, K. B., U.S. Pat. No. 4,683,202, issued 28 Jul. 1987.

Nishino, S., et al., *Nucleosides Nucleotides* 5:159 (1986).

Orson, F. M., et al., *Nucleic Acids Res.* 19:3435–3441 (1988).

Pegoraro, I., et al., *J. Natl. Cancer Inst.* 70:447–450 (1983).

Perlakey, L., et al., *Anti-Cancer Drug Design* 8:3–14 (1993).

Postel, E. H., et al., *Proc. Natl. Acad. Sci. USA* 88, 8227–8231 (1991).

Ratajczak, M. Z., et al., *Proc. Natl. Acad. Sci. USA* 89: 8474–8478 (1992).

Riley, M. J., et al., *J. Mol. Biol.* 20:359–398 (1966).

Rittner, K., et al., *Nucleic Acids Res.* 19:1421–1426, (1991).

Roy, S., et al., *Genes Dev.* 4:1365–1373 (1990).

Sambrook, J., et al., In *Molecular Cloning: A Laboratory Manual*, Cold Spring Harbor Laboratory Press, Vol. 2 (1989).

Sauer, Robert T., Editor, Methods in Enzymology *Protein/DNA Interactions*, Academic Press (1991).

Seelig, R., et al., *Leukemia* 7(1):1886–1887 (1993).

Shabarova, Z. A., *Biochemie* 70:1323–1334 (1988).

Stein, C. A. and Cheng, Y.-C., *Science* 261:1004–1012 (1993).

Szczylik, C., et al., *Science* 253: 562–565 (1991).

Tidd, D. M., et al., *Anti-Cancer Drug Design* 3:117–127 (1988).

Uhlman, E., et al., *Chem. Rev.* 90:544–584 (1990).

Vickers, T., et al., *Nuc. Acids Res.* 19(12):3359–3368 (1991).

Weeks, K. M., et al., *Science* 249:1281–1285 (1990).

Wickstrom, E., Editor, *Prospects for Antisense Nucleic Acid Therapy of Cancer and AIDS*, Wiley-Liss, New York, N.Y. (1991).

Wilson, W. D., et al., *Biochemistry* 32 (40):10614–10621 (1993).

Zalewski, A., et al., *Circulation Res.* 88:1190–1195 (1993).

Zamecnik, P. C., et al., *Proc. Natl. Acad. Sci. USA* 83:4143–4146 (1986).

Zielinski, W. S., et al., *Nucl. Acids Res.* 15:1699–1715 (1987).

BACKGROUND OF THE INVENTION

Oligonucleotides have been proposed as potent diagnostic compounds and as new rationally designed therapeutic agents (Uhlman, 1990; Helene, et al., 1990; Helene, 1991). The mechanism of action of these compounds is based on their specific interaction with RNA or DNA regions of interest.

Several modifications of the natural phosphodiester internucleoside bond {phosphomono(Eckstein, et al., 1985; Cohen, 1993) or dithioate (Marshall, et al., 1993), methylphosphonate (Miller, 1991), phosphodiester amidate (Letsinger, et al., 1988; Froehler, et al., 1988)} have been introduced to improve (i) the stability of the oligomers in biological media, and (ii) the hybridization properties of the oligomers.

Unfortunately, the vast majority of these analogs exhibit reduced binding with target RNA or DNA strands via duplex or triplex formation (Kibler-Herzog, et al., 1991). Moreover, the presence of the stereoisomers at phosphorous in some of these analogs may complicate the binding patterns with complimentary nucleic acids (LaPlauche, et al., 1986; Bower, et al., 1987; Tidd, et al., 1988).

SUMMARY OF THE INVENTION

Methods and compositions of the present invention relate to oligodeoxyribonucleotides having contiguous nucleoside subunits joined by intersubunit linkages. In the oligonucleotides, at least 2 contiguous subunits are joined by N3'→P5' phosphoramidate intersubunit, or greater than 3 of the total intersubunit linkages are N3'→P5' phosphoramidate intersubunit linkages.

An exemplary N3'→P5' phosphoramidate intersubunit linkage is shown in FIG. 2A, where X is —O⁻, —Or or —R, and R is selected from the group consisting of alkyl, alkenyl, aryl, and alkaryl. For definitions of these exemplary substituent groups see the Definitions section below.

The nucleoside subunits making up the oligodeoxyribonucleotides of the present invention can be selected to be in a defined sequence: such as, a sequence of bases complementary to a single-strand nucleic acid target sequence or a sequence that will allow formation of a triplex structure between the oligodeoxyribonucleotide and a target duplex.

In one embodiment the oligodeoxyribonucleotide has at least 3 contiguous subunits joined by N3'→P5' phosphoramidate linkages. This grouping of linkages can, for example, be located at the 3' end of the oligodeoxyribonucleotide. At this location the N3'→P5' phosphoramidate linkages confer nuclease resistance to the oligodeoxyribonucleotide.

In another embodiment of the present invention, all of the intersubunit linkages are N3'→P5' phosphoramidate linkages.

Also included in the invention are oligodeoxyribonucleotides where the intersubunit linkages alternate the N3'→P5' phosphoramidate linkage and a second linkage. The second linkage may be selected from one or more different types of linkages, for example, phosphodiester linkages or phosphodiester and phosphorothioate linkages. The second linkage is selected, for example, from the group consisting of phosphodiester, phosphotriester, methylphosphonate, phosphoramidate P3'→N5', and phosphorothioate. In one embodiment at least 50% of the intersubunit linkages are N3'→P5' phosphoramidate linkages.

The present invention includes a method for generating a triplex DNA molecule, comprising forming an oligodeoxyribonucleotide as described above, where the oligodeoxyribonucleotide has a sequence of nucleoside subunits effective to form triple-helix structure with a target duplex DNA. The oligodeoxyribonucleotide is then contacted with the duplex DNA under conditions effective to allow formation of a triplex between the oligodeoxyribonucleotide and the duplex target DNA. This method can be carried out under a variety of conditions, for example, intracellularly or in solution.

The present invention also includes a triplex DNA molecule, having three DNA strands: (i) a duplex DNA molecule, having two complementary strands, and (ii) bound to the duplex a third strand oligodeoxyribonucleotide having N3'→P5' phosphoramidate linkages as discussed above. In one embodiment, 50% or greater of the intersubunit linkages of the third strand oligodeoxyribonucleotide are N3'→P5' phosphoramidate linkages, including fully modified oligodeoxyribonucleotides.

Further, the invention includes a method of enhancing the resistance of an oligodeoxyribonucleotide to nuclease digestion. In this method an oligodeoxyribonucleotide is formed having N3'→P5' phosphoramidate linkages as described above. The oligodeoxyribonucleotide is exposed to nuclease. Such oligodeoxyribonucleotides are more resistant to nuclease digestion than a corresponding oligodeoxyribonucleotide having only phosphodiester intersubunit linkages. Nuclease resistance is observed intracellularly as well.

The oligodeoxyribonucleotides having N3'→P5' phosphoramidate linkages, as described above, have superior hybridization properties. The present invention also includes a method of enhancing hybridization of a first oligodeoxyribonucleotide to an RNA target sequence, where the oligodeoxyribonucleotide has contiguous nucleoside subunits joined by intersubunit linkages. In the method, a second oligodeoxyribonucleotide having N3'→P5' phosphoramidate linkages is formed having the same sequence of contiguous nucleoside subunits as the first oligodeoxyribonucleotide. The second oligodeoxyribonucleotide is effective to hybridize to said target RNA sequence. The second oligodeoxyribonucleotide is then contacted with the RNA under conditions effective to allow formation of a complex between the oligodeoxyribonucleotide and the RNA. Such contacting can be carried out under a variety of conditions, including intracellularly.

The present invention also includes a method and kit for the isolation of a target RNA from a sample. The kit includes an oligodeoxyribonucleotide having N3'→P5' phosphoramidate linkages, as described above, where the oligodeoxyribonucleotide is effective to hybridize to the target RNA sequence. Typically, the oligodeoxyribonucleotide is attached to a solid support, such as a magnetic bead, to facilitate isolation.

In another embodiment, the present invention includes a diagnostic method to detect the presence in a sample of an RNA having a selected target sequence. In this method, oligodeoxyribonucleotides having N3'→P5' phosphoramidate linkages are created that are effective to form a hybridization complex with a target sequence. The oligodeoxyribonucleotide is then contacted with the sample under conditions effective to allow formation of the hybridization complex between the oligodeoxyribonucleotide and the target sequence. The presence of the hybridization complex is then detected. Detection of the hybridization complex can be accomplished by labelling the oligodeoxyribonucleotide with a reporter moiety, where detecting includes detection of the reporter moiety. Numerous reporter moieties are available, including, but not limited to, radioactive labels, biotin labels, and fluorescent labels. This detection method can be carried out under a variety of conditions including intracellularly.

Similar diagnostic methods can be carried out using oligodeoxyribonucleotide having N3'→P5' phosphoramidate linkages, where the target sequences are duplex DNA or single-stranded DNA. In the case of detection of duplex DNA, detection of the hybridization complex can be accomplished using a gel band shift assay. For detection of single-stranded DNA the oligodeoxyribonucleotide typically contains greater than 50% of the total intersubunit linkages as N3'→P5' phosphoramidate intersubunit linkages.

The present invention also includes a duplex oligodeoxyribonucleotide, having (i) two complementary strands, and (ii) contiguous nucleoside subunits joined by intersubunit linkages, where at least 2 contiguous subunits are joined by N3'→P5' phosphoramidate intersubunit linkages, or greater than 3 of the total intersubunit linkages are N3'→P5' phosphoramidate intersubunit linkages (as described above). In one embodiment, 50% or greater of the intersubunit linkages of at least one strand are N3'→P5' phosphoramidate linkages. In another embodiment all of the intersubunit linkages of at least one strand are N3'→P5' phosphoramidate linkages. Such duplex DNA molecules may also include a flexible hinge region connecting the complementary strands. The hinge region may connect the strands in any desired polarity, e.g., 5' to 3', 3' to 5', 3' to 3', and 5' to 5'.

Further, the present invention includes a method of forming a triplex nucleic acid complex, having two complementary DNA strands and one RNA strand containing a target region, and compositions thereof. In the method, an oligodeoxyribonucleotide having contiguous nucleoside subunits joined by intersubunit linkages is formed. The oligodeoxyribonucleotide is capable of forming a duplex oligodeoxyribonucleotide, having (i) two complementary strands with 5' and 3' ends, (ii) contiguous nucleoside subunits joined by intersubunit linkages, where at least 2 contiguous subunits are joined by N3'→P5' phosphoramidate intersubunit, or greater than 3 of the total intersubunit linkages are N3'→P5' phosphoramidate intersubunit linkages (as described above), (iii) where the strands are connected from the end of one strand to the end of the other strand by a flexible hinge region, and (iv) the complementary oligodeoxyribonucleotide strands having a sequence of nucleoside subunits effective to form triple-helix structure with the RNA target. The oligodeoxyribonucleotide is then contacted with the RNA target under conditions effective to allow formation of a triplex between the oligodeoxyribonucleotide and the RNA. This method can be carried out under a variety of conditions, including, intracellularly.

The present invention also includes pharmaceutical compositions of oligodeoxyribonucleotides having N3'→P5' phosphoramidate linkages, as described above. The oligodeoxyribonucleotides are useful in therapeutic applications based on hybridization, such as, antigene and antisense applications.

These and other objects and features of the invention will be more fully appreciated when the following detailed description of the invention is read in conjunction with the accompanying drawings.

BRIEF DESCRIPTION OF THE FIGURES

In FIGS. 2D and 2F, R' is, for example, a lower alkyl group, other substitutions are possible as described by Goodchild (1990).

FIG. 3 presents exemplary oligonucleotides and $T_m$ values of duplexes and triplexes. In the figure:

$^a$=The $T_m$'s of complexes in the buffer A.

$^b$=T in the buffer; $T_m$ of the hairpin duplex was 55.7 and 61.5° C. in buffer A and B, respectively.

$^c$=Mismatched nucleotide is underlined.

Figure 4A:
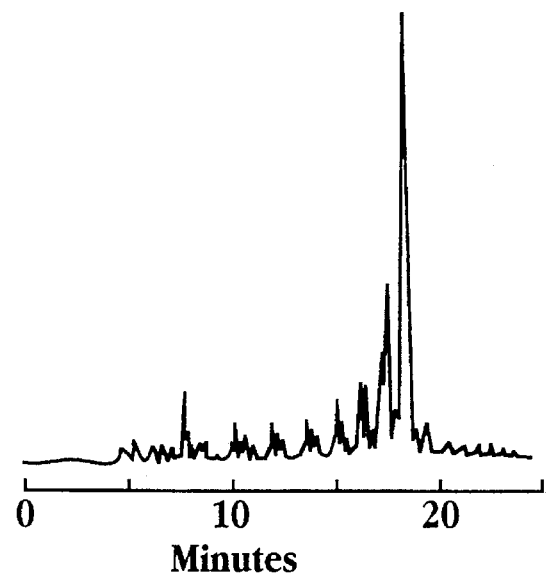
Figure 4B:
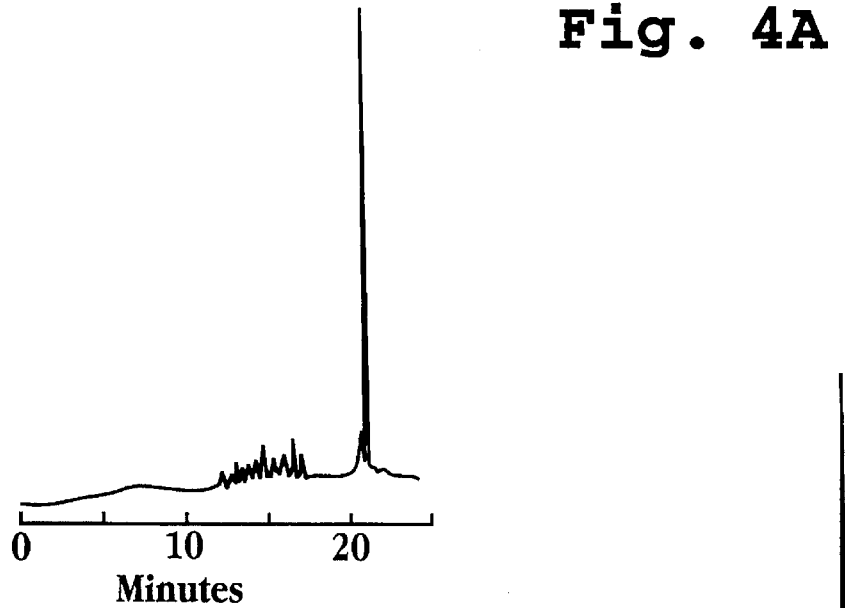
Figure 4C:
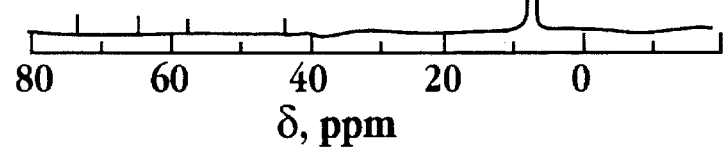

FIGS. 4A to 4C. FIG. 4A presents an IE HPLC profile of the reaction mixture after synthesis of the phosphoramidate Oligonucleotide SEQ ID NO:3. FIG. 4B presents a capillary gel electrophoresis profile of the reaction mixture after synthesis of the undecaphosphoramidate SEQ ID NO:6. FIG. 4C shows the results of $^{31}$P-NMR of the decaphosphoramidate 3.

Figure 5A:
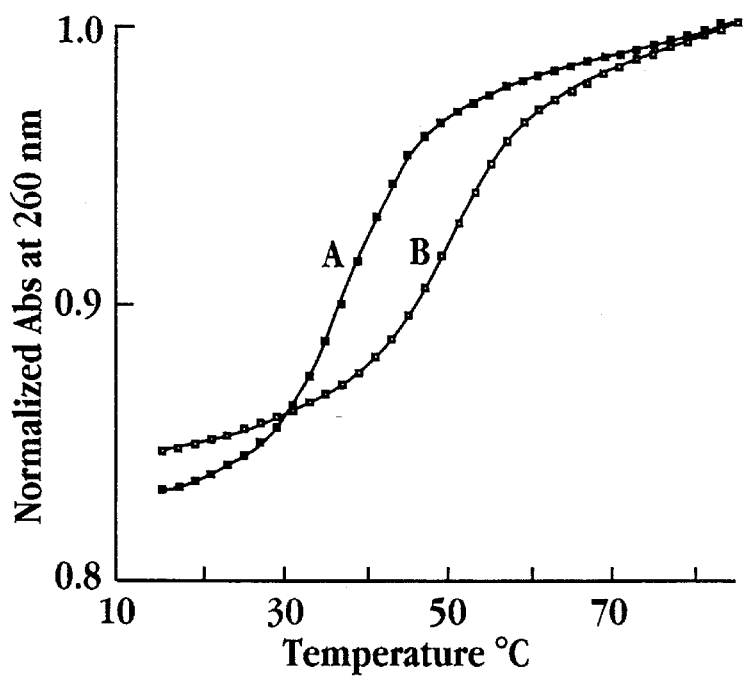
Figure 5B:
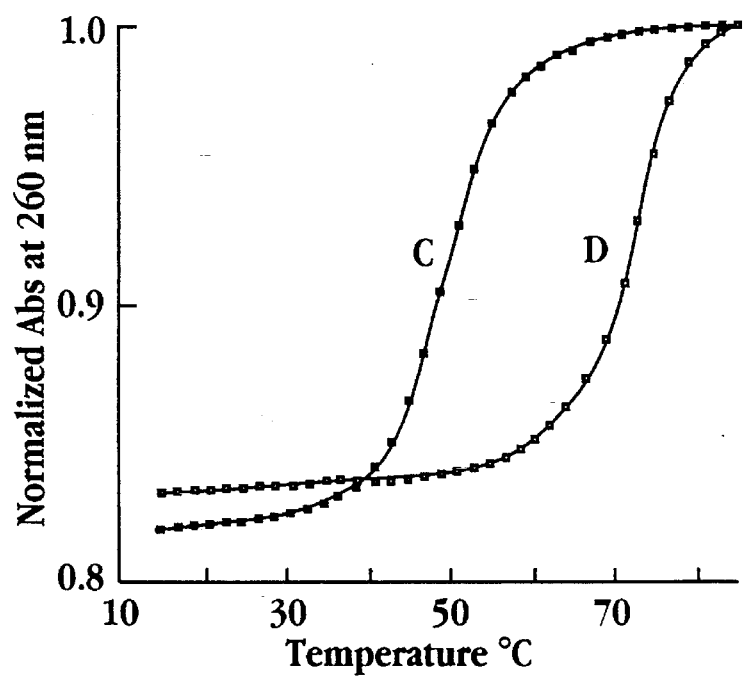

FIGS. 5A to 5B display melting curves for the duplexes, formed by phosphodiester and phosphoramidate oligomers.

FIG. 6 shows exemplary oligonucleotide hairpins and their $T_m$ values.

FIGS. 7A to 7D show melting curves for the triplexes.

Figure 8:
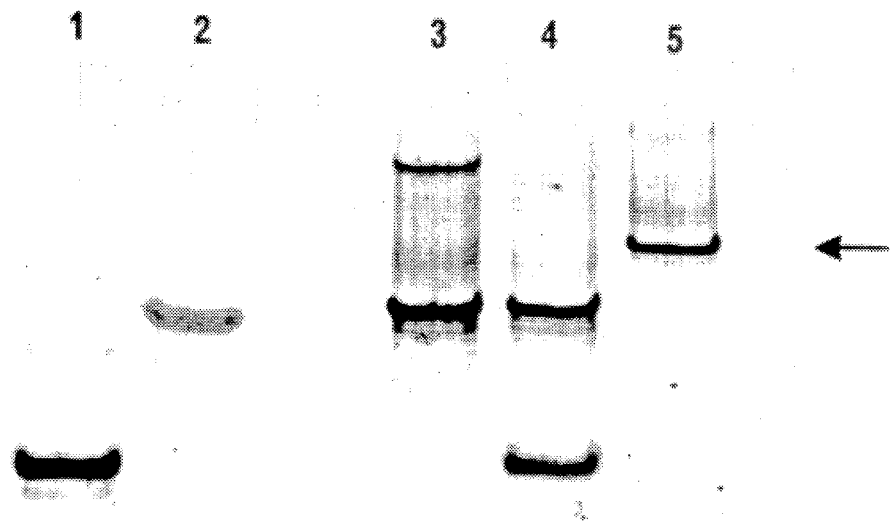

FIG. 8 shows gel-electrophoresis analysis of the oligonucleotide triplex formation under native conditions.

Figure 9:
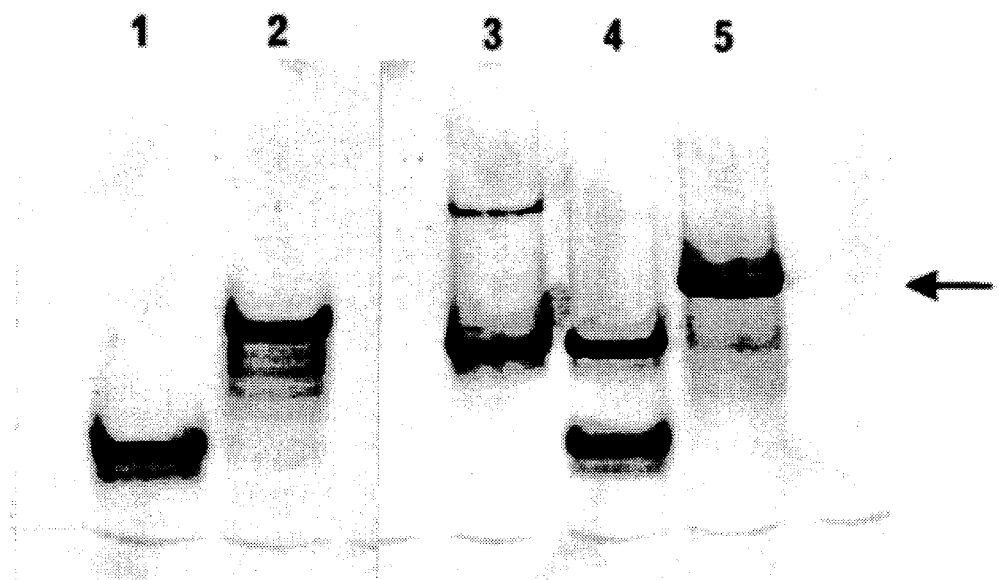

FIG. 9 shows gel-electrophoresis analysis of the oligonucleotide triplex formation under native conditions.

FIGS. 10 through 19 show the results of antisense oligonucleotides, having either phosphoramidate (N3'→P5') (FIGS. 10–15) or phosphorothioate (FIGS. 16–19) intersubunit linkages, on leukemia cell proliferation for different BCR-ABL leukemia cell lines and control cell lines.

Figure 20:
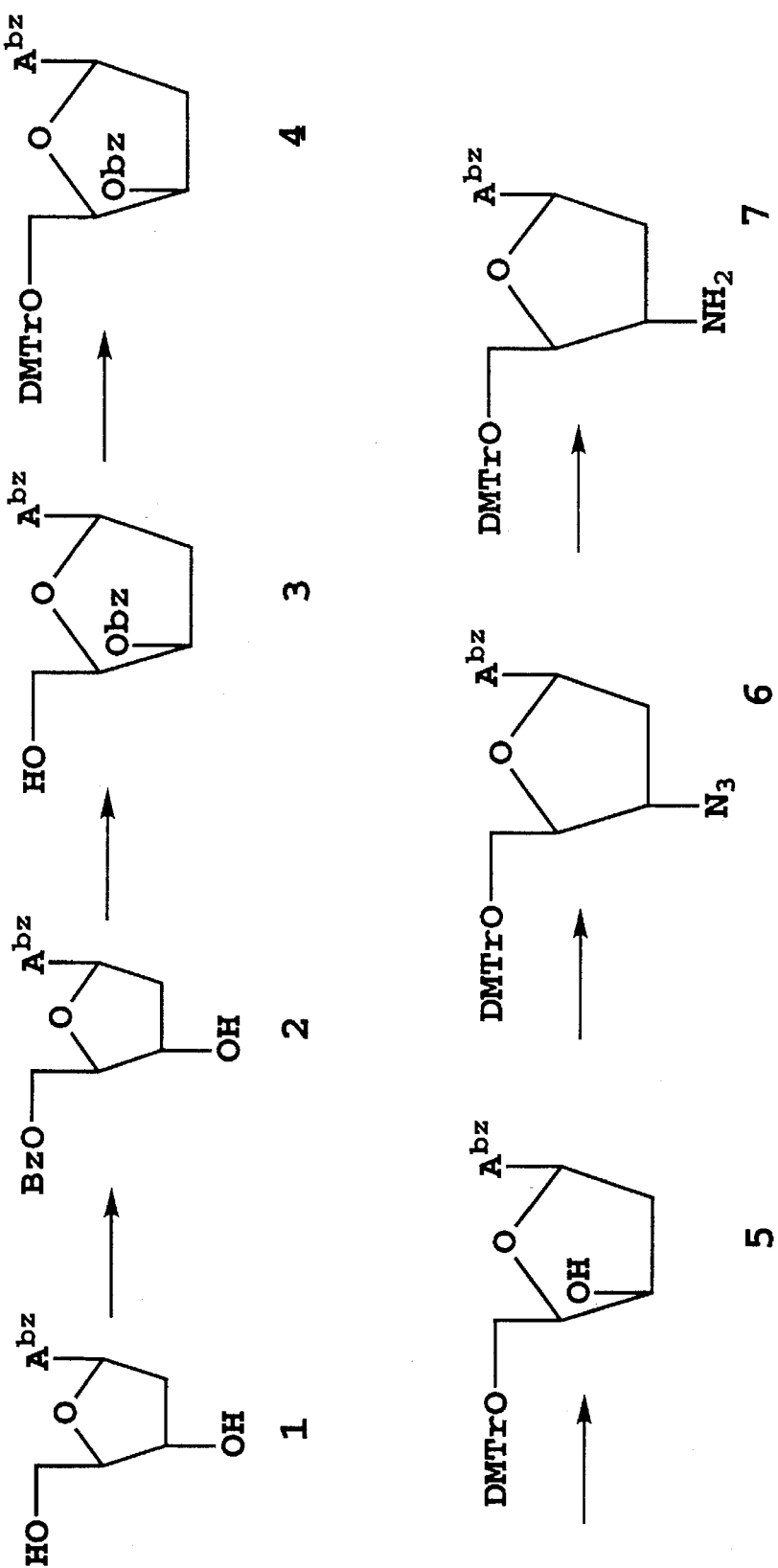

FIG. 20 schematically represents the preparation of 3'-amino-N$^6$-benzoyl-5'-dimethoxytrityl-2', 3'-dideoxyadenosine.

DETAILED DESCRIPTION OF THE INVENTION

I. DEFINITIONS

An "alkyl group" refers to an alkyl or substituted alkyl group having 1 to 20 carbon atoms, such as methyl, ethyl, propyl, and the like. Lower alkyl typically refers to $C_1$ to $C_5$. Intermediate alkyl typically refers to $C_6$ to $C_{10}$. Similarly, "cycloalkyl group" refers to a saturated carbocyclic ring group which may have alkyl, aryl, aralkyl substituents such as cyclopropyl, cyclopentyl, cyclohexyl, and the like, or a substituted form thereof.

An "alkenyl group" refers to a hydrocarbon group containing a carbon-carbon double bond, such as vinyl, allyl, cyclopentenyl, and the like. An "alkenyl group" also refers to substituted alkenyls.

An "aryl group" refers to an aromatic ring group having 5–20 carbon atoms, such as phenyl, naphthyl, anthryl, or substituted aryl groups, such as, alkyl- or aryl-substitutions like tolyl, ethylphenyl, biphenylyl, etc. Also included are heterocyclic aromatic ring groups having one or more nitrogen, oxygen, or sulfur atoms in the ring.

An "alkaryl group" refers to substituted alkyl group, such as, aryl-substitutions like benzyl, phenethyl, etc.

By "substituted" it is generally meant that the group is derivatized with one or more small chemical moieties, e.g., methoxy, ethoxy, halogen, hydroxyl, cyano, amido, amine and ethylene oxide. Any of the groups defined above may be substituted, for example, (—$CF_3$)

"Oligonucleotides" typically refer to nucleoside subunit polymers having between about 4 and about 50 contiguous subunits. The nucleoside subunits can be joined by a variety of intersubunit linkages, including, but not limited to, those shown in FIGS. 2A to 2E. Further, "oligonucleotides" includes modifications, known to one skilled in the art, to the sugar backbone (e.g., ribose or deoxyribose subunits), the sugar (e.g., 2' substitutions), the base, and the 3' and 5' termini. "Oligodeoxyribonucleotides" include such modifications, such as, 2' sugar substitutions of flourine.

"Nucleoside" is defined herein as a pentose sugar (a ribose, deoxyribose, or modification thereof) bound to a base capable forming hydrogen bonds (typically a purine or pyrimidine).

A "base" is defined herein to include (i) typical DNA and RNA bases (uracil, thymine, adenine, guanine, and cytosine), and (ii) modified bases or base analogs (e.g., 5-methyl-cytosine, 5-bromouracil, or inosine). A base analog is a chemical whose molecular structure mimics that of a typical DNA or RNA base.

II. THE PRESENT INVENTION

Experiments performed in support of the present invention demonstrate that oligonucleotides containing achiral internucleoside 3'-NHP(O)(O$^-$)O-5' phosphoramidate linkages (N3'→P5' ) are more resistant to nuclease digestion and have improved RNA and dsDNA hybridization characteristics relative to oligonucleotides not containing N3'→P5' phosphoramidate linkages. Oligonucleotides containing the N3'→P5' linkages have excellent antisense activity against complementary mRNA targets in in vitro cell growth inhibition assays. Further, the oligonucleotides exhibit low cytotoxicity.

A. SYNTHESIS AND CHARACTERIZATION OF OLIGONUCLEOTIDES CONTAINING INTERNUCLEOSIDE 3'-NHP(O)(O$^-$)O-5' PHOSPHORAMIDATE LINKAGES

Oligonucleotides, containing single N3'→P5' phosphoramidate linkage were prepared by chemical ligation in aqueous media (essentially as described by Shabarova, 1988). Alternatively, oligonucleotides containing N3'→P5' linkages between two subunits where the next intersubunit bond was at least one phosphodiester bond, were synthesized on a solid support via coupling of the preformed phosphoramidate dimer blocks (Gryaznov, et al., 1992; Mag, et al., 1992). Random size ribooligonucleotide N3'→P5' phosphoramidates were obtained via self-polymerization of dimer blocks (Zielinski, et al., 1987). Azhayer, et al., describe the synthesis of defined sequence oligoribonucleotides.

The present invention includes solid support synthesis methods for the generation of oligodeoxyribonucleotides with contiguous nucleoside subunits joined by N3'→P5' phosphoramidate intersubunit linkages (np) (Example 1, FIG. 1). Sequential synthesis of oligodeoxyribonucleotides utilizes 5'-dimethoxytrityl-3'-amino-deoxyribonucleotide subunits. The preparation of each of these subunits is described in Example 1 (see, for example, FIG. 20).

Oligonucleotides having contiguous subunits joined by N3'→P5' phosphoramidate intersubunit linkages (e.g., uniformly modified) were synthesized on a solid support using the step-by-step elongation procedure outlined in FIG. 1 (Example 1). The synthetic cycle for addition of a single aminonucleoside consists essentially of the following operations: detritylation (FIG. 1, step i); phosphitylation of the 5'-hydroxyl group to generate a polymer supported 5'-H-phosphonate diester (FIG. 1, steps ii, iii); Atherton-Todd type (Atherton, et al., 1945; Gryaznov, et al., 1992; Gryaznov, et al., 1986; Gryaznov, et al., 1990) coupling of a 5'-dimethoxytrityl-3'-amino nucleoside (Glinski, et al., 1970) with the 5'-H-phosphonate in the presence of carbon tetrachloride (FIG. 1, step iv). This cycle can be repeated several times resulting in phosphoramidate oligonucleotide after deprotection with ammonia (FIG. 1, step v, vi). Average coupling yields were 94–96% per step as judged by dimethoxytrityl (DMT) cation assay. Exemplary oligodeoxyribonucleotides containing N3'→P5' phosphoramidate linkages ("np" ) are presented in FIG. 3.

Oligodeoxyribonucleotides of the present invention contain at least two contiguous subunits joined by N3'→P5' phosphoramidate intersubunit linkages (for example, 5'-T-np-G-np-A-3'), or greater than 3 total N3'→P5' phosphoramidate intersubunit linkages. In one embodiment, the oligodeoxyribonucleotides contain fully modified N3'→P5' phosphoramidate intersubunit linkages (e.g., FIG. 3, experiment 13, oligonucleotide SEQ ID NO: 6). In another embodiment, the oligodeoxyribonucleotides have alternating N3'→P5' phosphoramidate intersubunit linkages between subunits, typically alternating with phosphodiester or phosphorothioate linkages (see exemplary linkages below and in FIG. 2). A example of such an oligodeoxyribonucleotide having alternating linkages is shown in FIG. 3, experiment 3, oligonucleotide 2. Synthesis of oligonucleotide SEQ ID NO:2 is described in Example 1.

Oligonucleotides were isolated by ion exchange high performance liquid chromatography (IE HPLC; Example 2, FIG. 4A). Purities of isolated oligonucleotide preparations were evaluated by capillary electrophoresis and slab gel electrophoresis analysis (Example 2, FIG. 4B).

Presence of the phosphoramidate linkages in the purified oligonucleotides was confirmed by $^{31}$P-NMR (Example 2, FIG. 4C) and by selective acid-catalyzed hydrolysis of phosphoramidate linkages (Example 2).

Figure 1A:
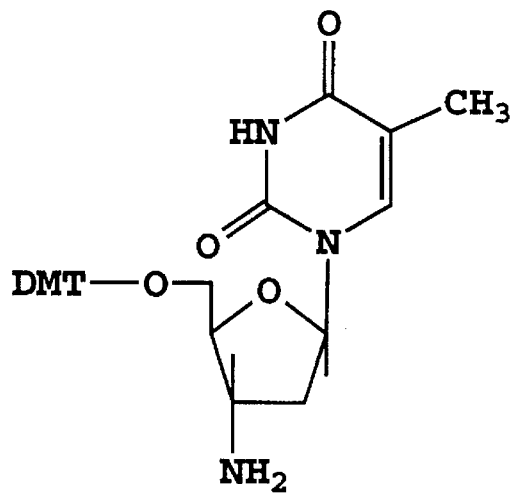
FIGS. 1A to 1D show the structures of subunits useful for the synthesis of oligonucleotides having internucleoside 3'-NHP(O)(O$^{31}$)O-5' phosphoramidate linkages (N3'→P5' ).
Figure 1B:
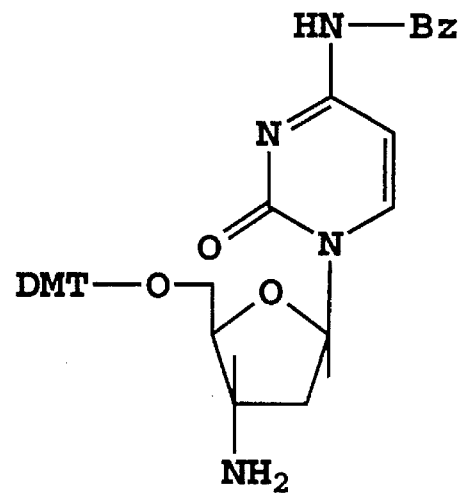
Figure 1C:
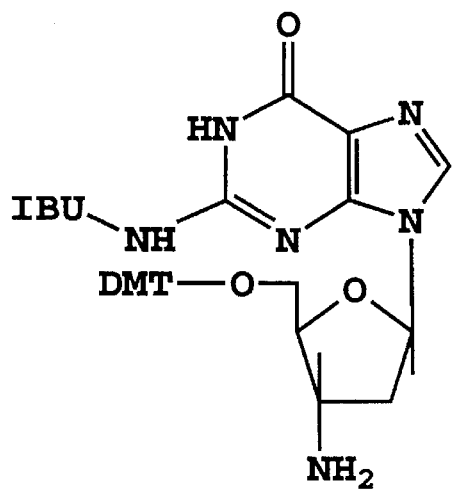
Figure 1D:
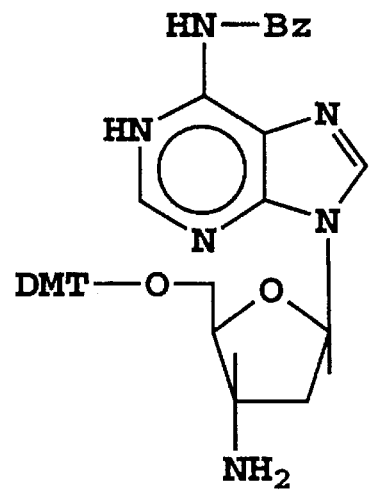
Figure 1E:
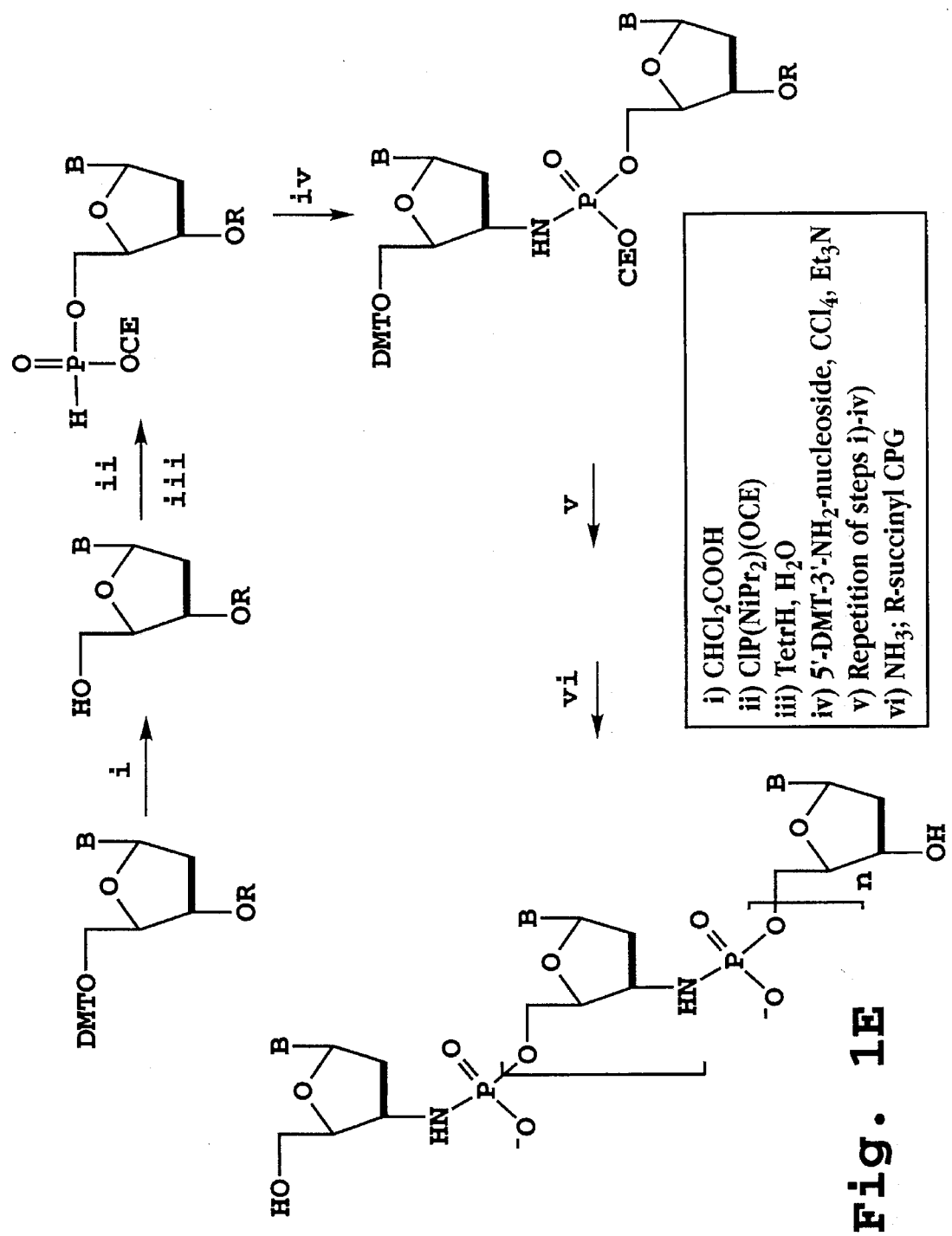
FIG. 1E shows a schematic outline of the step-by-step synthesis of uniformly modified oligonucleotides. In the figure, CE=cyanoethyl and CPG=controlled pore glass.
Figure 2A:
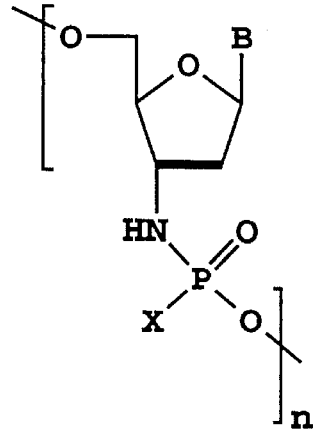
FIGS. 2A to 2E present exemplary combinations of 3'-NHP(O)(O$^-$)O-5' phosphoramidate intersubunit linkages with other, alternative linkages.
Figure 2B:
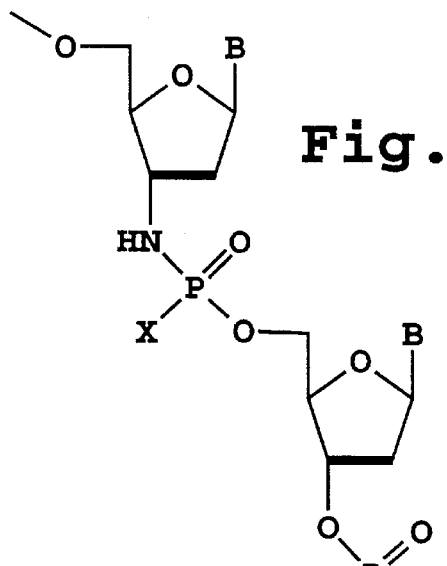
Figure 2C:
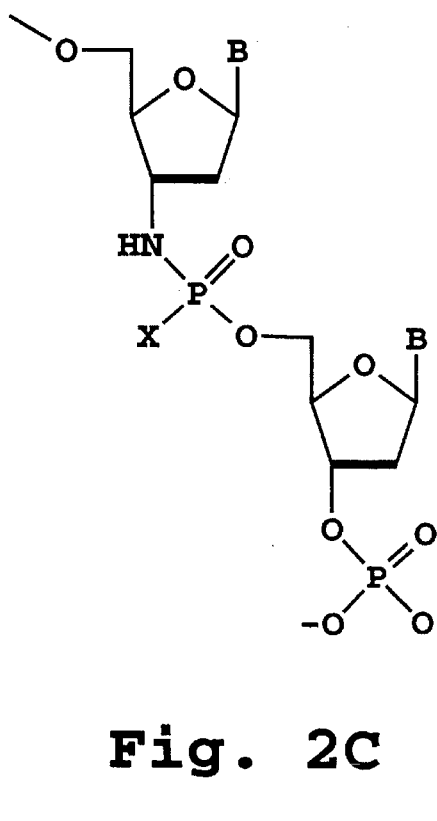
Figure 2D:
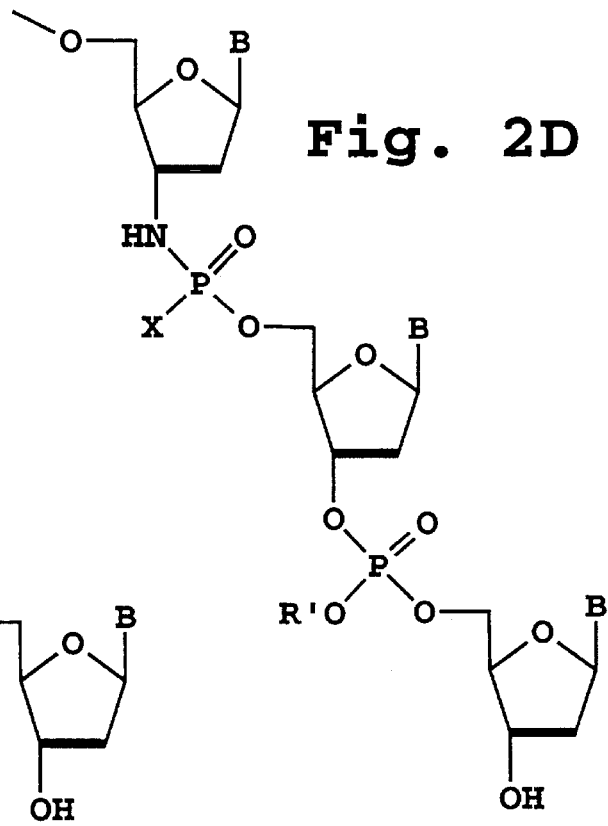

The cyanoester group in FIG. 1E (step i, iii) can be replaced by other pendent groups, including, alkyl (usually lower or intermediate alkyls), alkenyl, aryl and alkaryl groups (or substitutions of any of the preceding groups). Typically, such pendant groups do not interfere with the synthesis of oligonucleotides or the ability of the oligonucleotide to hybridize to a target. One exemplary pendent group is —CH$_3$ (Gryaznov, et al., 1992). A typical repeat unit is shown in FIG. 2A, where "X" is "—O—" "-OR" or "—R", and "R" is, for example, any of the following pendent groups or substitutions thereof: alkyl, alkenyl, aryl, and alkaryl.

Figure 2E:
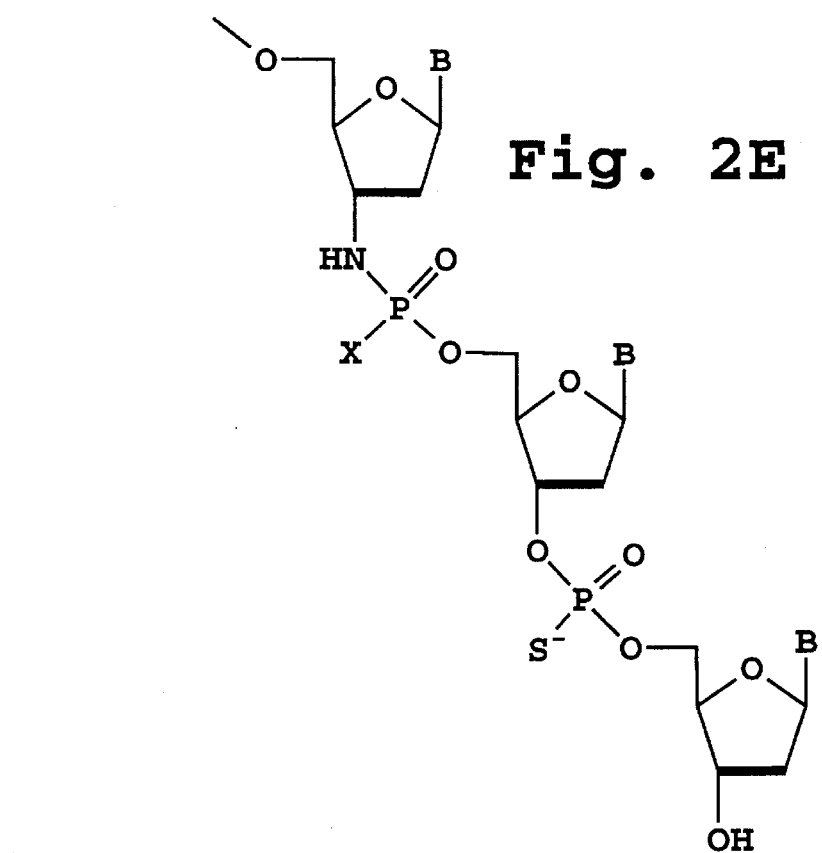
Figure 2F:
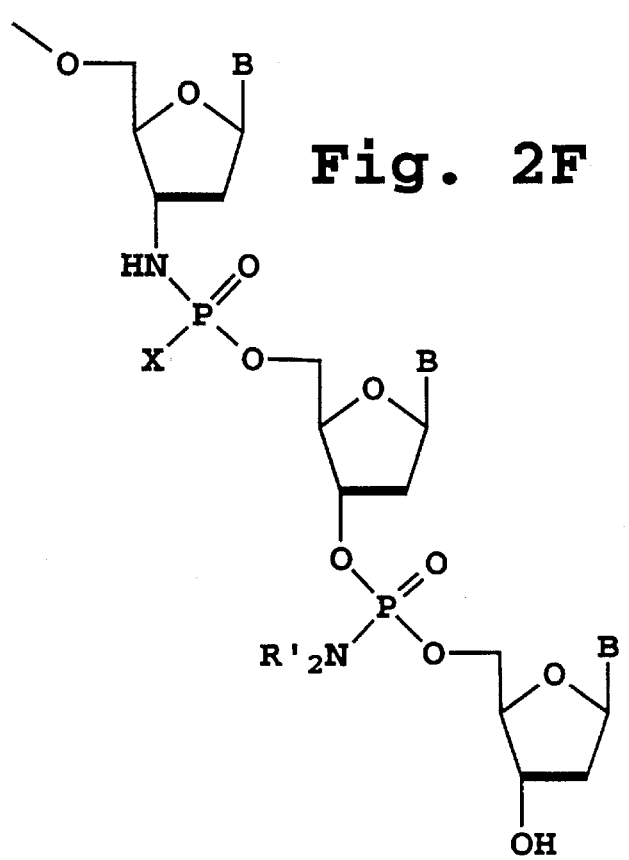

In addition to phosphoramidate analogs and chimeric phosphoramidate/phosphodiester analogs (FIG. 2C), the internucleoside N3'→P5' phosphoramidate linkages can be incorporated into oligonucleotides having one or more other modified intersubunit linkages (reviewed by Goodchild, 1990), including, but not limited to, phosphotriesters (FIG. 2D), methylphosphonates (FIG. 2B), phosphoramidates (FIG. 2F), phosphoramidates P3'→N5' and phosphorothioates (FIG. 2E)

B. NUCLEASE RESISTANCE OF OLIGONUCLEOTIDES CONTAINING ACHIRAL INTERNUCLEOSIDE 3'-NHP(O)(O⁻)O-5' PHOSPHORAMIDATE LINKAGES

Stability of the oligonucleotide phosphoramidates toward hydrolysis by snake venom phosphodiesterase was evaluated in comparison with natural phosphodiester compounds (see Materials and Methods) Phosphodiester decamer Oligonucleotide SEQ ID NO:1 (FIG. 3) was treated with snake venom phosphodiesterase. The oligonucleotide SEQ ID NO: 1 was completely hydrolyzed after 10 minutes, as judged by reversed phase high performance liquid chromatography HPLC.

In contrast, phosphoramidate analog Oligonucleotide SEQ ID NO:3 was essentially intact even after 50 minutes of treatment with snake venom phosphodiesterase. After 4.5 hours, approximately 50% of Oligonucleotide SEQ ID NO:3 was converted to the presumed 9-mer (TnpT)$_4$T$_{NH2}$ with a terminal 3'-amino group. The presence of the terminal 3'-amino group retarded further digestion of the oligomer. After 22 hours of hydrolysis, the starting 10-mer Oligonucleotide SEQ ID NO:3 was completely converted to the 3'-amino-terminal 9-mer {(TnpT)$_4$T$_{NH2}$}. Only about 20% further digestion of the {(TnpT)$_4$T$_{NH2}$} compound was observed.

These results demonstrate the increased nuclease resistance of oligonucleotides containing N3'→P5' phosphoramidate linkages ("np"), relative to oligonucleotides having standard phosphodiester backbones. In one embodiment of the present invention, nuclease resistance of oligodeoxyribonucleotides is generated by placing approximately 3 contiguous subunits linked by N3'→P5' phosphoramidate intersubunit linkages at the 3' end of the oligodeoxyribonucleotides.

C. HYBRIDIZATION PROPERTIES OF OLIGONUCLEOTIDES CONTAINING N3'→P5' PHOSPHORAMIDATE LINKAGES

The hybridization properties of the phosphoramidate analogs were evaluated relative to complementary DNA or RNA strands having standard phosphodiester intersubunit linkages. The thermal stability data for duplexes generated from phosphoramidate analogs and phosphodiester oligomers are summarized in FIG. 3 (Example 1).

Exemplary melting curve data (Example 4A) for duplexes formed by phosphodiester and phosphoramidate analog oligomers are presented in FIGS. 5A and 5B. In the figures, curves (A), (C), (B), and (D) correspond to experiments 8, 9, 13 and 14 in FIG. 3, respectively.

Substitution of the internucleoside phosphodiester for the N3'→P5' phosphoramidate linkages dramatically changed the oligonucleotides' hybridization properties. Melting temperatures $T_m$'s of duplexes formed by the entirely modified 10-mer Oligonucleotide SEQ ID NO:3 with poly Da (i.e., DNA) and poly A (i.e., RNA) were 36.0° C. and 51.5° C., respectively (FIG. 3, experiments 5 and 6). These Tm's are 6.3° C. and 24.5° C. higher than duplexes formed by the phosphodiester counterpart Oligonucleotide SEQ ID NO:1 with poly Da and poly A (FIG. 3, experiments 1 and 2).

The same trend is true for the mixed-base undecanucleotide SEQ ID NO:6 (FIG. 3), where the $T_m$'s of duplexes with complementary DNA and RNA strands were 49.2° C. and 72.4° C., respectively, (FIG. 3, experiments 13, 14). These values are 11.7° C. and 22.9° C. higher than for the parent phosphodiester compound Oligodeoxyribonucleotide 4 (FIG. 3, experiments 8 and 9). Also, the duplex with the same RNA target formed by phosphoramidate 11-mer Oligodeoxyribonucleotide SEQ ID NO:6 is more stable (by 18.0° C.) than one formed by the homologous RNA oligomer SEQ ID NO:5 (FIG. 3, experiment 1).

Oligodeoxyribonucleotide SEQ ID NO:2, with alternating phosphodiester - phosphoramidate linkages, also binds more tightly with the RNA strand, $T_m$ 33.7° C. (FIG. 3, experiment 4) than the corresponding phosphodiester compound (Oligodeoxyribonucleotide SEQ ID NO:1, FIG. 3, experiment 2). However, Oligodeoxyribonucleotide SEQ ID NO:2 binds less strongly with the DNA template, $T_m$ 25.8° C., (FIG. 3, experiment 3) relative to its phosphodiester counterpart (Oligodeoxyribonucleotide SEQ ID NO:1, FIG. 3, experiment 1).

Hybridization of the phosphoramidate oligonucleotides with complementary nucleic acids is sequence specific and determined by the proper Watson-Crick base pairing. The duplex formed by phosphoramidate Oligodeoxyribonucleotide SEQ ID NO:6 with single mismatched RNA target (FIG. 3, experiment 15) is substantially less stable ($\Delta T_m$ –12.2° C.) than the duplex formed with the fully complementary RNA oligomer (FIG. 3, experiment 13). About the same mismatch discrimination was observed for the phosphodiester deoxyribo- and ribo- oligonucleotides, where $\Delta T_m$ was –14.4° C. and –12.4° C. respectively (FIG. 3, experiments 10, 12).

A previous study with phosphoramidate analogs demonstrated that introduction of three N3'→P5' phosphoramidate linkages resulted in a destabilization trend, relative to two such linkages, for heteroduplexes formed with deoxyribo-oliognucleotide targets (Gryaznov, et al., 1992). In contrast to the prior art trend, the results presented above demonstrate that typically having up to 50% of the intersubunit linkages as phosphoramidate linkages decreases the stability of DNA/DNA heteroduplexes. Greater than 50% phosphoramidate intersubunit linkages in one strand of a DNA duplex, however, begins to improve stability of the duplex relative.

When a DNA duplex is formed between a normal, phosphodiester oligonucleotide and an oligonucleotide fully modified with N3'→P5' phosphoramidate linkages, the thermal stability of the duplex is much higher than the corresponding duplex having only phosphodiester linkages in both strands (FIG. 3, compare experiments 1 and 5).

Gryaznov, et al. (1992) only contains data concerning the hybridization properties of DNA/DNA duplexes where one strand contains up to three N3'→P5' phosphoramidate linkages (non-contiguous). In sharp contrast to the teachings of the prior art concerning DNA targets, experiments performed in support of the present invention demonstrate that having increasing numbers of phosphoramidate analog linkages present in an oligodeoxyribonucleotide increases the stability of DNA/RNA heteroduplexes. To achieve DNA/RNA heteroduplex stabilization, a preferred embodiment of the present invention includes an oligodeoxyribonucleotide having at least 2 contiguous, or more than 3 total intersubunit linkages modified to have N3'→P5' phosphoramidate linkages.

Experiments were also performed to evaluate the stability of duplexes formed by oligonucleotides containing phosphoramidate linkages in both complementary strands. Several chimeric phosphoramidate-phosphodiester hairpin oligomers (FIG. 6) were synthesized (FIG. 6, Example 4B) having Thymidine-containing hinge regions ($T_4$, FIG. 6). Melting curves obtained for these compounds show that the most stable duplexes were formed by the hairpins in Oligonucleotides SEQ ID NO:9 and SEQ ID NO: 2—where both strands contain phosphoramidate linkages in opposing positions (FIG. 6, experiments 3, 6).

Also, duplexes formed from single-strand DNA molecules (i.e., hairpins) where one strand contains alternating phosphoramidate-phosphodiester linkages and the complementary strands has only phosphodiester linkages, are more stable than their solely phosphodiester counterparts (FIG. 6, experiments 1, 4).

These results suggest that when both strands of a DNA/DNA duplex contain phosphoramidate analog linkages, the duplex is stabilized by the presence of N3'→P5' phosphoramidate linkages in each strand. Stable duplexes can be formed with one phosphoramidate linkage in each strand— in one embodiment the phosphoramidate linkage is in the same location in each strand.

To achieve DNA/DNA duplex stabilization typically 2 or more of the intersubunit linkages in each DNA strand of a duplex forming oligonucleotide are modified to have N3'→P5' phosphoramidate linkages. In one embodiment, one strand of a hairpin forming DNA oligonucleotide can be modified to have about 50–100% of N3'→P5' phosphoramidate intersubunit linkages.

D. TRIPLEX FORMATION USING PHOSPHORAMIDATE ANALOGS

The ability of the phosphoramidate analogs to form triplexes with double-stranded DNA was also evaluated (Example 4). Melting curves were obtained for triplexes formed by the decathymidilic phosphoramidate Oligodeoxyribonucleotide SEQ ID NO:6 and the $dA_{10}$:$dT_{10}$ duplex region of the hairpin DNA target $d(A_{10}C_4T_{10})$ (FIG. 3, experiment 7). The triplex had a $T_m$ of 32° C. at close to physiological conditions. A more stable triplex ($T_m$ 42.2° C.) was observed in magnesium-containing buffer (FIG. 3, experiment 7).

The same $T_m$ value was obtained for triplexes formed by phosphoramidate Oligonucleotide SEQ ID NO:3 with poly Da:poly Dt duplex. Thermal dissociation of the triplexes was monitored by change of absorbance at 260 nm (FIGS. 7A and 7C), as well as at 284 nm (FIGS. 7B and 7D), which is characteristic for T:AT triplexes (Riley, et al., 1966).

Results of the gel-shift experiments under native conditions also demonstrate formation of the stable triplex by phosphoramidate decamer SEQ ID NO:3 and dsdna target (FIG. 8), as well as stable triplex formation by Oligonucleotide SEQ ID NO:6 (FIG. 9).

Under the same hybridization conditions neither phosphodiester decathymidilic acid Oligonucleotide SEQ ID NO:1, nor Oligonucleotide SEQ ID NO:4 formed triplexes with the same double-stranded DNA targets, as judged by the melting curves and by the gel-shift experiments (FIG. 8). That is, no corresponding triplex was formed by the oligonucleotides which have phosphodiester intersubunit linkages—suggesting that the phosphoramidate analogs may more readily form triplexes than their phosphodiester containing counterparts.

Similar results were obtained when Oligonucleotide SEQ ID NO:6 and Oligonucleotide SEQ ID NO:1 were evaluated for their ability to form triplex structures with duplex DNA targets (Example 5, FIG. 9).

The results presented above suggest that the phosphoramidate oligonucleotides are more effective for triplex formation, with a duplex substrate, than standard phosphodiester oligonucleotides.

III. APPLICATIONS OF OLIGONUCLEOTIDES CONTAINING INTERNUCLEOSIDE 3'-NHP (O) (O⁻) O-5' PHOSPHORAMIDATE LINKAGES

Oligonucleotide SEQ ID NO:3 '-NHP(O) (O⁻)O-5' phosphoramidates were synthesized. These compounds are nuclease resistant and form surprisingly stable complexes with ssRNA and DNA targets. The N3'→P5' phosphoramidate analogs have great potential for anti-sense and anti-gene diagnostic/therapeutic applications. In a preferred embodiment of the present invention, the oligonucleotides are oligodeoxyribonucleotides.

A. ANTI-SENSE APPLICATIONS

Antisense therapy involves the administration of exogenous oligonucleotides that bind to a target nucleic acid, typically an RNA molecule, located within cells. The term antisense is so given because the oligonucleotides are typically complementary to mRNA molecules ("sense strands") which encode a cellular product.

The phosphoramidate analog oligonucleotides described herein are useful for antisense inhibition of gene expression (Matsukura et al., 1989; Agrawal et al., 1989; Zamecnik et al., 1986; Rittner and Sczakiel, 1991; Stein and Cheng, 1993). Oligonucleotides containing N3'→P5' phosphoramidate linkages have therapeutic applications for a large number of medically significant targets, including, but not limited to inhibition of cancer cell proliferation and interference with infectious viruses. The N3'→P5' phosphoramidate oligonucleotides are useful for both veterinary and human applications. The low cytotoxicity of these compounds and their ability to act effectively as antisense molecules at low concentrations (see below) make these oligonucleotides highly desirable as therapeutic antisense agents.

Anti-sense agents typically need to continuously bind all target RNA molecules so as to inactivate them or alternatively provide a substrate for endogenous ribonuclease H (Rnase H) activity. Sensitivity of RNA/oligonucleotide complexes, generated by the methods of the present invention, to Rnase H digestion can be evaluated by standard methods (Donia, et al., 1993; Kawasaki, et al., 1993).

The methods of the present invention provide several advantages over the more conventional antisense agents. First, phosphoramidate analog oligonucleotides bind more strongly to RNA targets than corresponding phosphodiester oligonucleotides. Second, the phosphoramidate analog oligonucleotides are more resistant to degradation by cellular nucleases. Third, in cellular uptake of the compound, an uncharged phosphoramidate analog backbone may allow more efficient entry of the phosphoramidate analog oligonucleotides into cells than a charged oligonucleotide.

Further, when an RNA is coded by a mostly purine strand of a duplex target sequence, phosphoramidate analog oligonucleotides targeted to the duplex also have potential for inactivating the DNA—i.e., the ability to inactivate a pathogen in both single-stranded and double-stranded forms (see discussion of anti-gene therapies below).

Sequence-specific phosphoramidate analog binding molecules are potentially powerful therapeutics for essentially any disease or condition that in some way involves RNA. Exemplary modes by which such sequences can be targeted for therapeutic applications include:

a) targeting RNA sequences expressing products involved in the propagation and/or maintenance infectious agents, such as, bacteria, viruses, yeast and other fungi, for example, a specific mRNA encoded by an infectious agent;

b) formation of a duplex molecule that results in inducing the cleavage of the RNA (e.g., Rnase H cleavage of RNA/DNA hybrid duplex molecules);

c) blocking the interaction of a protein with an RNA sequence (e.g., the interaction of TAT and TAR, see below); and d) targeting sequences causing inappropriate expression or proliferation of cellular genes: for example, genes associated with cell cycle regulation; inflammatory processes; smooth muscle cell (SMC) proliferation, migration and matrix formation (Liu, et al., 1989); certain genetic disorders; and cancers (protooncogenes). In one embodiment, translation or RNA processing of inappropriately expressed cellular genes is blocked.

Exemplary potential target sequences are protooncogenes, for example, including but not limited to the following: c-myc, c-myb, c-fos, c-kit, ras, and BCR/ABL (e.g., Wickstrom; Zalewski, et al., 1993; Calabretta, et al., 1992, 1993;), oncogenes/tumor suppressor genes (e.g., p53, Bayever, et al.), transcription factors (e.g., NFκB, Cogswell, et al., 1993) and viral genes (e.g., papillomaviruses, Cowsert, et al.; herpes simplex virus, Kulka, et al.). To further illustrate, two RNA regions of the HIV-1 protein that can be targeted by the methods of the present invention are the REV-protein response element (RRE) and the TAT-protein transactivation response element (TAR). REV activity requires the presence of the REV response element (RRE; SEQ ID NO:23), located in the HIV envelope gene (Malim et al., 1989a, 1989b).

The RRE has been mapped to a 234-nucleotide region thought to form four stem-loop structures and one branched stem-loop structure (Malim et al., 1989a). Data obtained from footprinting studies (Holland et al., 1990; Kjems et al., 1991) suggest that REV binds to six base pairs in one stem structure and to three nucleotides in an adjacent stem-loop structure of the RRE. A minimum REV binding region of about 40 nucleotides in stem-loop II has been identified by Cook, et al. (1991; SEQ ID NO:24). This binding region can be target for generation of RNA/DNA duplexes (e.g., Li, et al., 1993) using one or more oligonucleotides, according to the methods of the present invention.

The HIV-1 TAT is essential for viral replication and is a potent transactivator of long terminal repeat (LTR)-directed viral gene expression (Dayton et al., 1986; Fisher et al., 1986). Transactivation induced by TAT protein requires the presence of the TAR element (SEQ ID NO:25) which is located in the untranslated 5' end of the viral mRNA element.

The TAR element is capable of forming a stable stem-loop structure (Muesing et al., 1987). The integrity of the stem and a 3 nucleotide (nt) bulge on the stem of TAR has been demonstrated to be essential for specific and high-affinity binding of the TAT protein to the TAR element (Roy et al., 1990; Cordingley et al., 1990; Dingwall et al., 1989; Weeks et al., 1990). This region can be targeted for anti-sense therapy following the method of the present invention.

In addition to targeting the RNA binding sites of the REV, RRE and TAT proteins, the RNA coding sequences for the REV and TAT proteins themselves can be targeted in order to block expression of the proteins.

Initial screening of N3'→P5' phosphoramidate oligonucleotides, directed to bind potential antisense target sites, typically includes testing for the thermal stability of resultant RNA/DNA duplexes. When a phosphoramidate analog oligonucleotide is identified that binds a selected RNA target sequence, the analog is further tested for inhibition of RNA function in vitro. Cell culture assays systems are used for such in vitro analysis (e.g., herpes simplex virus, Kulka, et al.; HIV-1, Li, et al., Vickers, et al.; coronary smooth muscle cell proliferation in restenosis, Zalewski, et al.; IL-2R, Grigoriev, et al.; c-myb, Baer, et al.; c-fos, Cutry, et al.; BCR/ABL, Szczylik, et al., 1991).

Example 5 presents the results of testing phosphoramidate oligonucleotides in one such cell culture system. The assay measures selective inhibition of leukemia cell proliferation by BCR-ABL antisense oligonucleotides (Szczylik, et al., 1991). BCR-ABL transcripts are found in the majority of chronic myelogenous leukemia (CML) patients and in $Ph^+$ acute lymphocytic leukemia patients, and are believed to be necessary for the maintenance of leukemic phenotype (Gale, et al.; Collins, et al., 1984; Daley, et al.). The BCR-ABL transcripts are the result of a translocation of the protooncogene ABL (chromosome 9) to the breakpoint cluster region (BCR) (chromosome 22), resulting in the formation of BCR-ABL hybrid genes.

A fully modified N3'→P5' phosphoramidate anti-sense oligonucleotide 11-mer (SEQ ID NO:6), complementary to the identified BCR-ABL junction B2A2 (cell line BV173), was synthesized and purified. A corresponding oligonucleotide 16mer (SEQ ID NO:26), (i) containing the 11mer sequence as given above, and (ii) having fully modified phosphorothioate intersubunit linkages, was also prepared. The oligonucleotides were administered to the cells at 24 hour intervals for three days (days 0, 1 and 2) at the concentrations shown in FIGS. 10 to 15, 16 and 18. Concentrations in the figures are presented as follows: 40/20/20 corresponds to concentrations, in µg/ml, of oligonucleotides as added to the cell cultures (Example 5).

Figure 17:
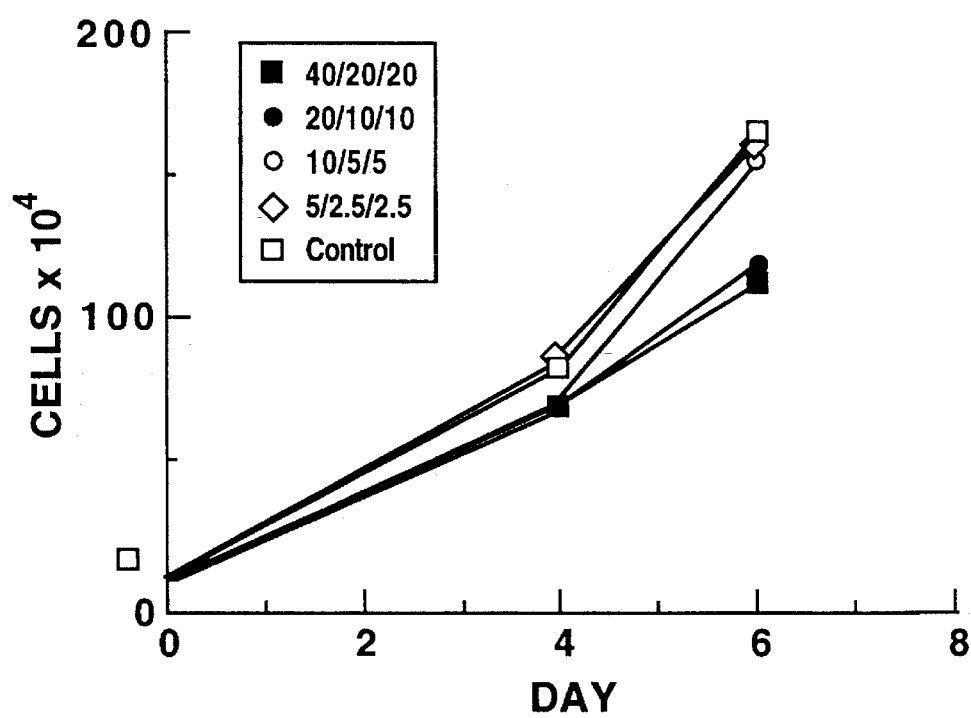
Figure 18:
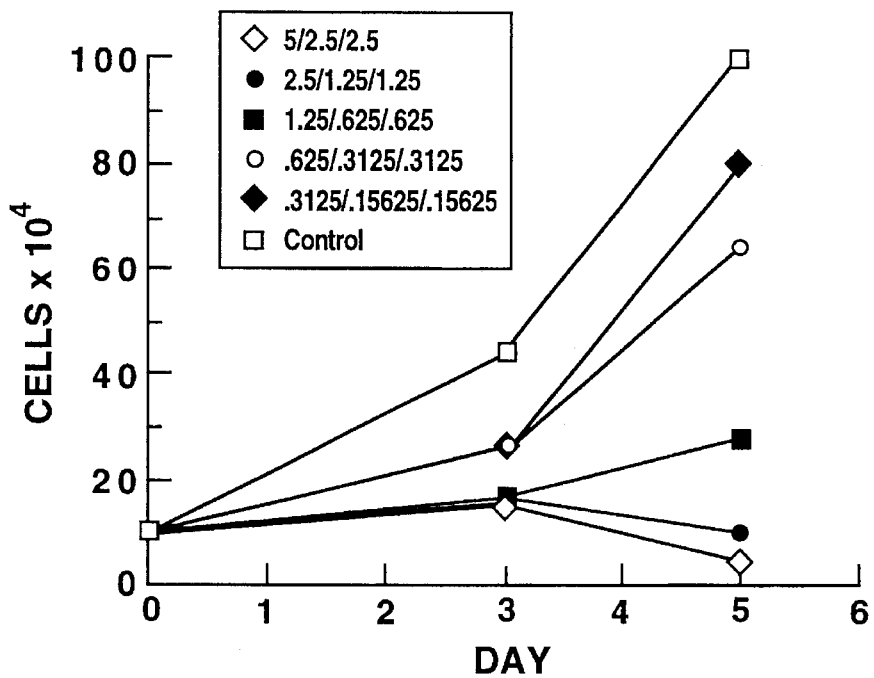

FIGS. 17 and 18 present the results for experiments performed using a 16mer, having fully modified phosphorothioate intersubunit linkages, with sequence mismatches to the BV173 BCR/ABL splice junction.

Figure 10:
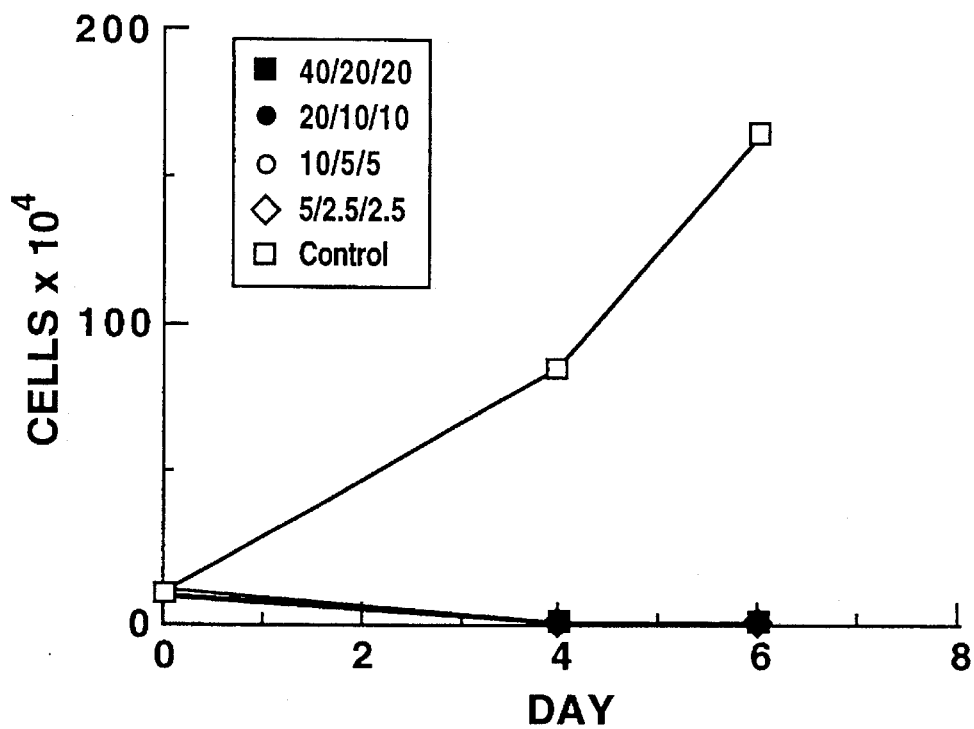
Figure 12:
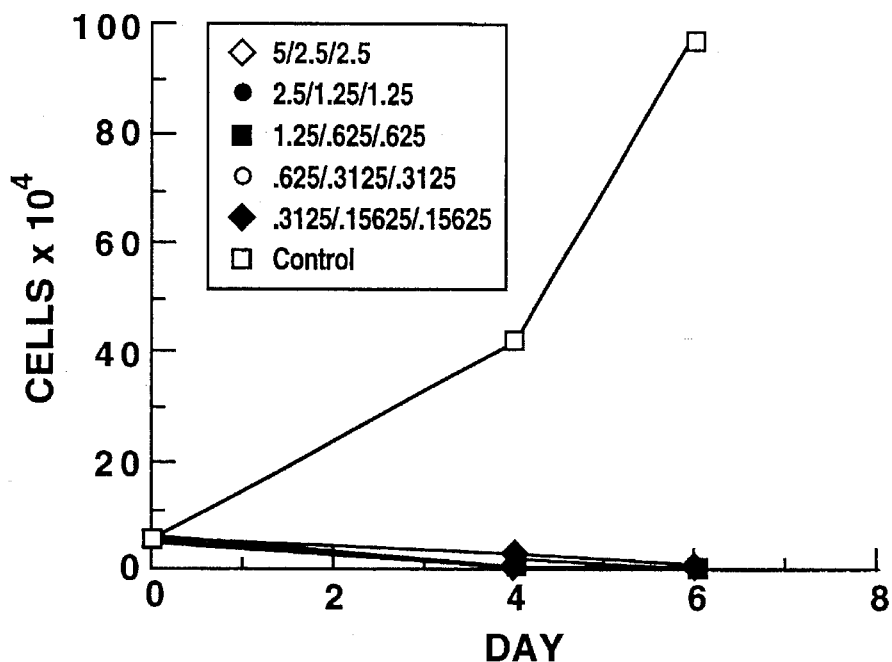
Figure 14:
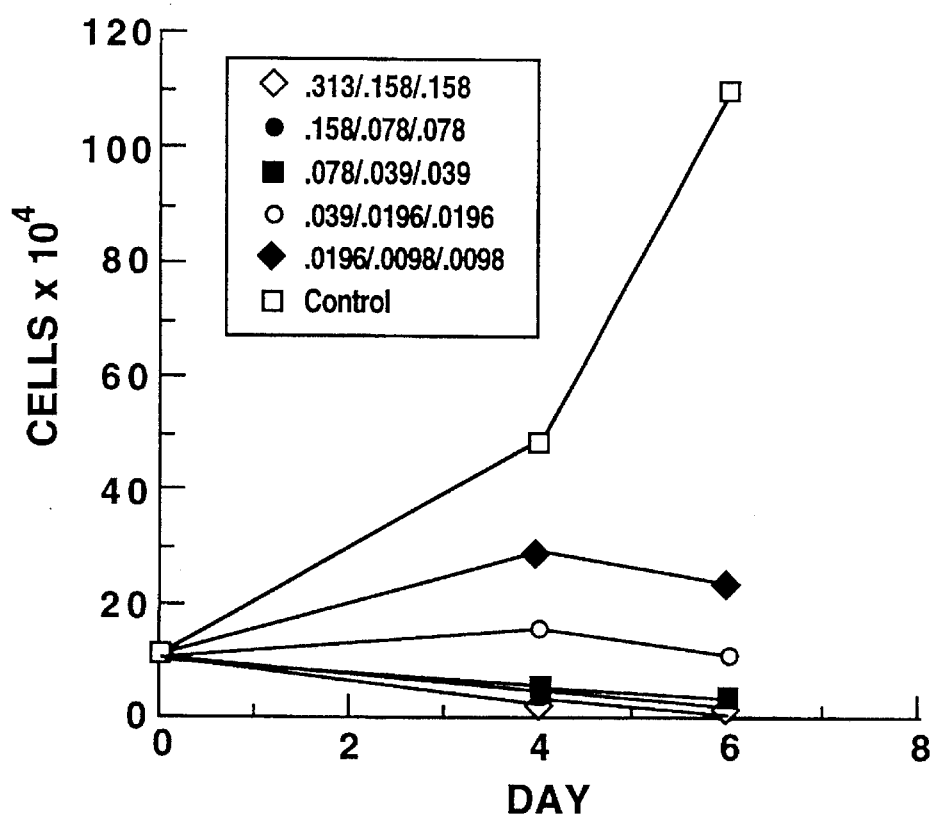

The results presented in FIGS. 10, 12 and 14 demonstrate that the phosphoramidate oligonucleotides were extremely effective at inhibiting BV173 leukemia cell proliferation, regardless of the concentration at which the oligonucleotide was administered.

Figure 11:
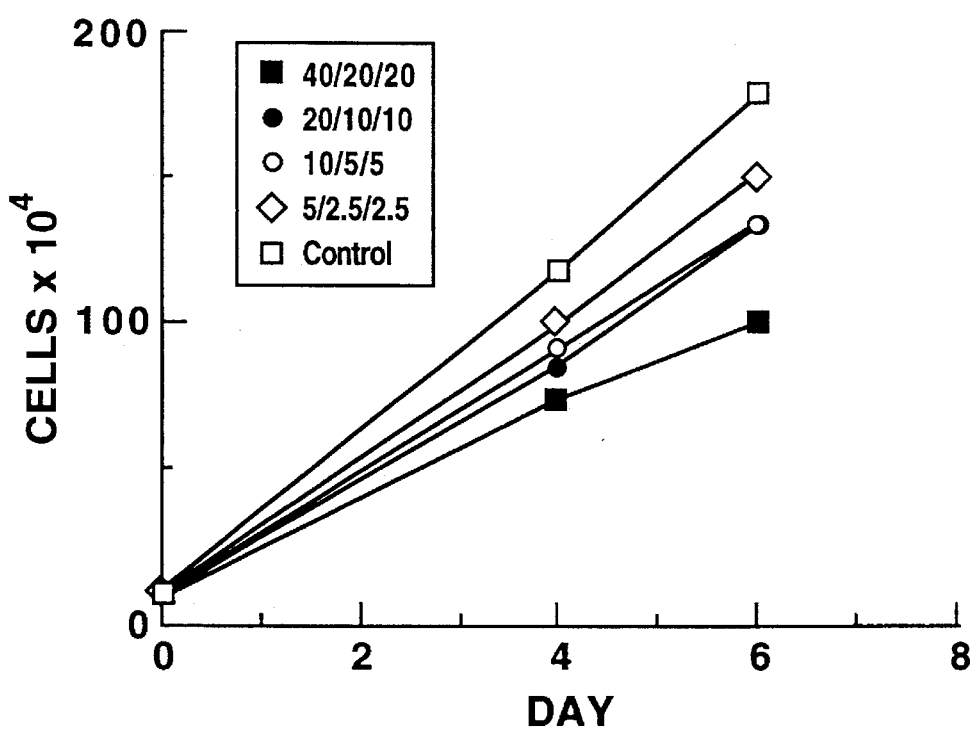
Figure 13:
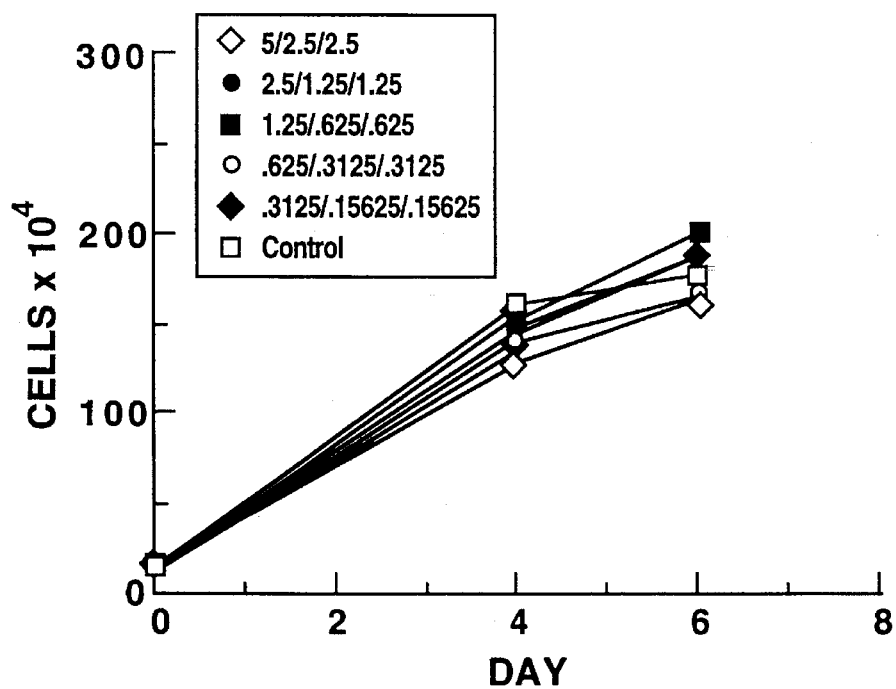
Figure 15:
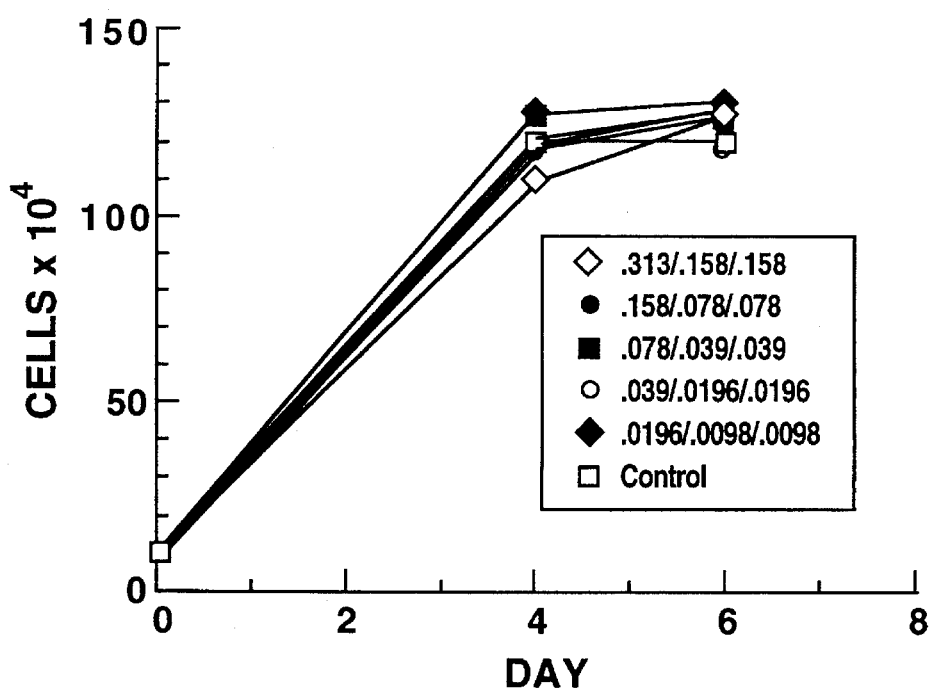

The results presented in FIGS. 11, 13 and 15 demonstrate that the phosphoramidate oligonucleotides have negligible cytotoxicity. In these experiments, the cell line was either HL60, which contains no BCR/ABL breakpoint, or K562, which contains the B3A2 BCR/ABL break point, which is partly non-homologous to the B2A2 BCR/ABL break point.

Figure 16:
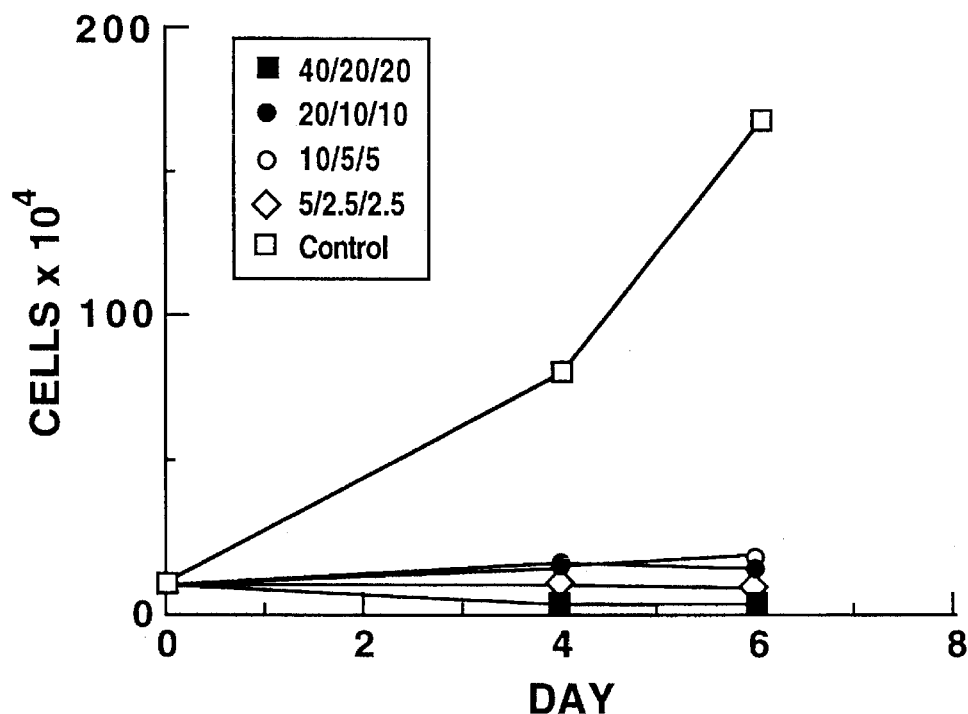

On the other hand, when similar experiments were performed using the phosphorothioate 16mer, the oligonucleotides were not effective at inhibiting BV173 leukemia cell proliferation when administered at comparable concentrations to the phosphoramidate oligonucleotide (FIGS. 16 and 18). Specifically, leukemia cells appear to begin to be released from inhibition by the phosphorothioate 16mer at a concentration of about 1.25/0.625/0.625 compared to a similar release of inhibition seen when using the phosphoramidate oligonucleotide at 0.0196/0.0098/0.0098. Accordingly, the results demonstrate that the phosphoramidate oligonucleotides are effective antisense agents at considerably lower concentrations than the widely used phosphorothioate oligonucleotides.

Further, the inhibition curves seen with the phosphoramidate oligonucleotide treatment have a downward inflection at later time points, even after the partial release of inhibition (FIG. 14). On the other hand, the inhibition curves seen with the phosphorothioate oligonucleotide treatment have a steep upward inflection at later time points, after the partial release of inhibition (FIG. 18). These results suggest that the release from inhibition is more dramatic for the phosphorothioate oligonucleotides when compared to the phosphoramidate oligonucleotides.

The absence of cytotoxicity with the phosphorothioate 16mer was comparable to that seen with the phosphoramidate oligonucleotide applied at the same concentration.

The results presented above confirm in cell culture the superior qualities of the N3'→P5' phosphoramidate oligonucleotides demonstrated by the hybridization studies described above. These results support the usefulness and efficacy of the N3'→P5' phosphoramidate oligonucleotides in antisense and antigene in vivo therapies.

Further, the results demonstrate that the N3'→P5' phosphoramidate oligonucleotides provide superior antisense function in vitro than phosphorothioate oligonucleotides. To date, the phosphorothioate backbone modification in oligonucleotides has become the standard for antisense applications, representing the subject analog in more than 95% of the ~2500 antisense journal publications in 1993.

In a great variety of assay systems involving a large number of mRNA targets, the antisense phosphorothioate oligonucleotides were required at concentrations of 1–15 μM in order to achieve substantial inhibitory effects. Nevertheless, inhibitory activity at that level was sufficient to commence US FDA approved clinical trials in three diseases targeting three different mRNAs: CML (chronic myelogenous leukemia), IND #42974 and AML (acute myelogenous leukemia) IND #40453 (Antiviral Agents Bulletin, Vol. 5, No. 6, pp161–162 (1992), ISSN 0897-9871, Biotechnology Information Institute); as well as Hepatitis B Virus (HBV).

The data presented in Example 5 demonstrate that the N3'→P5' phosphoramidate oligonucleotides are effective antisense agents at much lower concentrations than corresponding phosphorothioates. Further, the N3'→P5' phosphoramidate oligonucleotides have no apparent cytotoxicity even at the highest concentrations used, which were well above the concentrations required for antisense activity. The results indicate that the N3'→P5' phosphoramidate oligonucleotides are excellent agents for therapeutic applications.

In vitro effects of a selected phosphoramidate analog oligonucleotide can be confirmed in an in vivo system. Such in vivo systems include, but are not limited to, the following (target—model system): hepatitis virus—chimpanzee or monkey models; c-myb, c-myc, bcr-abl—SCID mouse models (e.g., Ratajczak, et al.); NF-κB—mouse (Higgins, et al.); and p120—mouse (Perlakey, et al.).

B. ANTI-GENE APPLICATIONS

Inhibition of gene expression via triplex formation has been previously demonstrated (Cooney et al., 1989; Orson et al., 1991; Postel et al., 1991). The increased stability of triplex structures formed when employing third strand phosphoramidate analog oligonucleotides provides a stronger tool for antigene applications, including veterinary and human therapeutic applications.

A target region of choice is selected based on known sequences using standard rules for triplex formation (Helene and Toulme, 1990). Typically, the phosphoramidate analog nucleic acid sequence is targeted against double-stranded genetic sequences in which one strand contains predominantly purines and the other strand contains predominantly pyrimidines.

Phosphoramidate analog oligonucleotides of the present invention are tested for triplex formation against a selected duplex target sequences using band shift assays (Example 4). Typically, high percentage polyacrylamide gels are used for band-shift analysis and the levels of denaturing conditions (Ausubel et al.; Sauer et al.; Sambrook et al.) are adjusted to reduce any non-specific background binding.

The duplex target is labeled (for example, using a radioactive nucleotide) and mixed with a third strand oligonucleotide, being tested for its ability to form triplex structures with the target duplex. A shift of the mobility of the labelled duplex oligonucleotide indicates the ability of the oligonucleotide to form triplex structures.

Triplex formation is indicated in the band shift assay by a decreased mobility in the gel of the labeled triplex structure relative to the labeled duplex structure.

Numerous potential target sites can be evaluated by this method including target sites selected from a full range of DNA sequences that vary in length as well as complexity. Sequence-specific phosphoramidate analog binding molecules are potentially powerful therapeutics for essentially any disease or condition that in some way involves DNA. Exemplary target sequences for such therapeutics include: a) DNA sequences involved in the propagation and/or maintenance infectious agents, such as, bacterial, viruses, yeast and other fungi, for example, disrupting the metabolism of an infectious agent; and b) sequences causing inappropriate expression or proliferation of cellular genes, such as oncogenes, for example, blocking or reducing the transcription of inappropriately expressed cellular genes (such as genes associated with certain genetic disorders).

Gene expression or replication can be blocked by generating triplex structures in regions to which required regulatory proteins (or molecules) are known to bind (for example, HIV transcription associated factors like promoter initiation sites and SP1 binding sites, McShan, et al.). Alternatively, specific sequences within protein-coding regions of genes (e.g., oncogenes) can be targeted as well.

When a phosphoramidate analog oligonucleotide is identified that binds a selected duplex target sequence tests, for example, by the gel band shift mobility assay described above, the analog is further tested for its ability to form stable triplex structures in vitro. Cell culture and in vivo assay systems, such as those described above under "Anti-Sense Applications" are used.

Target sites can be chosen in the control region of the genes, e.g., in the transcription initiation site or binding regions of regulatory proteins (Helene and Toulme, 1990; Birg et al., 1990; Postel et al., 1991; Cooney et al., 1988). Also, target sites can be chosen such that the target also exists in mRNA sequences (i.e., a transcribed sequence), allowing oligonucleotides directed against the site to function as antisense mediators as well (see above).

Also, phosphoramidate modified DNA molecules can be used to generate triplex molecules with a third strand target (i.e., a single-strand nucleic acid). For example, a DNA molecule having two regions capable of forming a triplex structure with a selected target third strand molecule can be synthesized. Typically the two regions are linked by a flexible region which allows the association of the two regions with the third strand to form a triplex. One example of such a DNA molecule is $T_{10}$(fully phosphoramidate modified)-(hinge region)-$T_{10}$(phosphodiester linkages). This molecule forms triplex structures with a polyA RNA target. A corresponding DNA molecule having $T_{10}$(phosphodiester linkages)-$C_4$(hinge region)-$T_{10}$(phosphodiester linkages) does not form triplex with a polyA RNA target.

Hinge regions can comprise any flexible linkage that keeps the two triplex forming regions together and allows them to associate with the third strand to form the triplex. Third strand targets are selected to have appropriate purine/pyrimidine content so as to allow formation of triplex molecules.

The flexible linkage may connect the two triplex forming regions (typically, complementary DNA strands) in any selected orientation depending on the nature of the base sequence of the target. For example, the two triplex forming regions each have 5' and 3' ends, these ends can be connected by the flexible hinge region in the following orienatations: 5' to 3', 3' to 5', 3' to 3', and 5' to 5'.

Further, duplex DNA molecules containing at least one phosphoramidate linkage in each strand can be used as decoy molecules for transcription factors or DNA binding proteins (e.g., c-myb).

Single-stranded DNA can also be used as a target nucleic acid for oligonucleotides of the present invention, using, for example, phosphoramidate intersubunit linkage-containing hairpin structures (e.g., FIG. 6). Two phosphoramidate analog oligonucleotides can be selected for single-strand DNA target-directed binding. Binding of the two phosphoramidate analog strands to the single-strand DNA target results in formation of a triplex.

C. PHARMACEUTICAL COMPOSITIONS.

The present invention includes pharmaceutical compositions useful in antisense and antigene therapies. The compositions comprise an effective amount of N3'→P5' phosphoramidate oligonucleotides in combination with a pharmaceutically acceptable carrier. One or more N3'→P5' phosphoramidate oligonucleotides (having different base sequences) may be included in any given formulation.

The N3'→P5' phosphoramidate oligonucleotides, when employed in therapeutic applications, can be formulated neat or with the addition of a pharmaceutical carrier. The pharmaceutical carrier may be solid or liquid. The formulation is then administered in a therapeutically effective dose to a subject in need thereof.

Liquid carriers can be used in the preparation of solutions, emulsions, suspensions and pressurized compositions. The N3'→P5' phosphoramidate oligonucleotides are dissolved or suspended in a pharmaceutically acceptable liquid carrier such as water, an organic solvent, a mixture of both, or pharmaceutically accepted oils or fats. The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators. Suitable examples of liquid carriers for parenteral administration of N3'→P5' phosphoramidate oligonucleotides preparations include water (partially containing additives, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil).

For parenteral administration of N3'→P5' phosphoramidate oligonucleotides the carrier can also be an oily ester such as ethyl oleate and isopropyl myristate. Sterile carriers are useful in sterile liquid form compositions for parenteral administration.

Sterile liquid pharmaceutical compositions, solutions or suspensions can be utilized by, for example, intraperitoneal injection, subcutaneous injection, intravenously, or topically. For example, antisense oligonucleotides directed against retinal cytomegalovirus infection may be administered topically by eyedrops. N3'→P5' phosphoramidate oligonucleotides can be also be administered intravascularly or via a vascular stent impregnated with mycophenolic acid, for example, during balloon catheterization to provide localized anti-restenosis effects immediately following injury.

The liquid carrier for pressurized compositions can be halogenated hydrocarbon or other pharmaceutically acceptable propellent. Such pressurized compositions may also be lipid encapsulated for delivery via inhalation. For administration by intranasal or intrabronchial inhalation or insufflation, N3'→P5' phosphoramidate oligonucleotides may be formulated into an aqueous or partially aqueous solution, which can then be utilized in the form of an aerosol, for example, for treatment of infections of the lungs like *Pneumocystis carnii*.

N3'→P5' phosphoramidate oligonucleotides may be administered topically as a solution, cream, or lotion, by formulation with pharmaceutically acceptable vehicles containing the active compound. For example, for the treatment of genital warts.

The N3'→P5' phosphoramidate oligonucleotides may be administered in liposome carriers. The use of liposomes to facilitate cellular uptake is described, for example, in U.S. Pat. No. 4,897,355 (Eppstein, D., et al., issued 30 Jan 1990) and 4,394,448 (Szoka, F,, et al., issued 19 Jul. 1983). Numerous publications describe the formulation and preparation of liposomes.

The dosage requirements for treatment with N3'→P5' phosphoramidate oligonucleotides vary with the particular compositions employed, the route of administration, the severity of the symptoms presented, the form of N3'→P5' phosphoramidate oligonucleotides and the particular subject being treated.

In general, N3'→P5' phosphoramidate oligonucleotides are administered at a concentration that affords effective results without causing any harmful or deleterious side effects (e.g., an effective amount). Such a concentration can be achieved by administration of either a single unit dose, or by the administration of the dose divided into convenient subunits at suitable intervals throughout the day.

D. DIAGNOSTIC APPLICATIONS

The phosphoramidate analog oligonucleotides are also useful in diagnostic assays for detection of RNA or DNA having a given target sequence. In one general application, the phosphoramidate analogs are labeled (e.g., isotopically or other detectable reporter group) and used as probes for DNA or RNA samples that bound to a solid support (e.g., nylon membranes).

Alternatively, the phosphoramidate analog oligonucleotides may be bound to a solid support (for example, magnetic beads) and homologous RNA or DNA molecules in a sample separated from other components of the sample based on their hybridization to the immobilized phosphoramidate analogs. Binding of phosphoramidate analogs to a solid support can be carried out by conventional methods. Presence of the bound RNA or DNA can be detected by standard methods, for example, using a second labeled reporter or polymerase chain reaction (Mullis; Mullis, et al.).

Diagnostic assays can be carried out according to standard procedures, with suitable adjustment of the hybridization conditions to allow phosphoramidate analog hybridization to the target region. The ability of phosphoramidate analog oligonucleotides to bind at elevated temperature can also help minimizes competition for binding to a target sequence between the phosphoramidate analog probe and any corresponding single-strand phosphodiester oligonucleotide that is present in the diagnostic sample.

D. OTHER APPLICATIONS

In one aspect, the phosphoramidate analog oligonucleotides can be used in methods to enhance isolation of RNA or DNA from samples. For example, as discussed above, phosphoramidate analogs can be fixed to a solid support and used to isolate complementary nucleic acid sequences, for example, purification of a specific mRNA from a polyA fraction (Goldberg, et al). The phosphoramidate analogs are advantageous for such applications since they can form more stable interactions with RNA and duplex DNA than standard phosphodiester oligonucleotides.

A large number of applications in molecular biology can be found for reporter labeled phosphoramidate analogs, particularly for the detection of RNA in samples. Phosphoramidate analogs can be labeled with radioactive reporters ($^3$H $^4$C $^{32}$P, or $^{35}$S nucleosides), biotin or fluorescent labels (Gryaznov, et al.). Labelled phosphoramidate analog oligonucleotides can be used as efficient probes in, for example, RNA hybridization reactions (Ausubel, et al., Sambrook, et al.).

Also, double-stranded DNA molecules where each strand contains at least one phosphoramidate linkage can be used for the isolation of DNA-duplex binding proteins. In this embodiment the duplex containing phosphoramidate intersubunit linkages is typically affixed to a solid support and sample containing a suspected binding protein is then passed over the support under buffer conditions that facilitate the binding of the protein to its DNA target. The protein is typically eluted from the column by changing buffer conditions.

The triplex forming DNA molecules described above, containing phosphoramidate modified linkages, can be used as diagnostic reagents as well, to, for example, detect the presence of an RNA molecule in a sample.

Further, complexes containing oligodeoxyribonucleotides having N3'→P5' phosphoramidate intersubunit linkages can be used to screen for useful small molecules or binding proteins: for example, N3'→P5' phosphoramidate oligodeoxyribonucleotide complexes with duplex DNA can be used to screen for small molecules capable of further stabilizing the triplex structure. Similar screens are useful with N3'→P5' phosphoramidate oligodeoxyribonucleotide complexes formed with single strand DNA and RNA molecules.

F. VARIATIONS

Variations on the phosphoramidate analog oligonucleotides used in the methods of the present invention include modifications to facilitate uptake of the oligonucleotide by the cell (e.g., the addition of a cholesterol moiety (Letsinger, 1990); production of chimeric oligonucleotides using other intersubunit linkages (Goodchild); modification with intercalating agents (for example, triplex stabilizing intercalating agents, Wilson, et al., 1993); and use of ribose instead of deoxyribose subunits.

Further modifications include, 5' and 3' terminal modifications to the oligonucleotides (e.g., —OH, —OR, —NHR, $NH_2$ and cholesterol). In addition, the ribose 2' position can be the site of numerous modifications, including, but not limited to, halogenation (e.g., —F).

N3'→P5' phosphoramidate oligonucleotides may also be modified by conjugation to a polypeptide that is taken up by specific cells. Such useful polypeptides include peptide hormones, antigens and antibodies. For example, a polypeptide can be selected that is specifically taken up by a neoplastic cell, resulting in specific delivery of N3'→P5' phosphoramidate oligonucleotides to that cell type. The polypeptide and oligonucleotide can be coupled by means known in the art (see, for example, PCT International Application Publication No. PCT/US89/02363, WO8912110, published Dec. 14, 1989, Ramachandr, K, et al.).

The properties of such modified phosphoramidate analog oligonucleotides, when applied to the methods of the present invention, can be determined by the methods described herein.

While preferred embodiments, uses, and methods of practicing the present invention have been described in detail, it will be appreciated that various other uses, formulations, and methods of practice as indicated herein are within the contemplation of the present invention.

MATERIALS AND METHODS

The methyl and cyanoethyl phosphoramidates and the H-phosphate nucleoside reagents were purchased from Glen Research (Sterling, Va.) and Applied Biosystems Inc., (Foster City, Calif.) Nucleoside methylphosphonoamidite reagents were purchased from Glen Research, and DMT-dT-LCAA CPG, 500 Å, was purchased from Applied Biosystems Inc.

For enzymatic hydrolysis of oligonucleotides, 0.2 $A_{260}$ units of a selected oligonucleotide and 0.22 U of phosphodiesterase from Crotalus durissus (Boehringer-Mannheim, Indianapolis, Ind.) were incubated for in 100 µl 10 mM Tris.HCl and 10 mM $MgCl_2$. Samples were taken for analysis at 0', 10', 40', 4.5 hours and 22 hours after addition of the phosphodiesterase. Products were analyzed by RP HPLC essentially as described in Example 2D.

Standard nucleic acid chemistry, including chemical synthesis of nucleic acids, has been reviewed by Miller (1990).

Chemicals were purchased from Aldrich (Milwaukee, Wis.), Sigma (St. Louis, Mo.) and Calbiochem (San Diego, Calif.).

HPLC was typically carried out using a Dionex chromatograph (Sunnyvale, Calif.). A "HYPERSIL ODS" column (4.6×200 mm, 5µ particle size; Hewlett Packard, Palo Alto, Calif.) and a 0.5%/minute gradient of $CH_3CN$ in 0.05M TEAH buffer, pH 7.0, were used for RP HPLC. For ion exchange chromatography, a Dionex "OMNI PAK" NA 100 column (4×250 mm) was used with a 1%/minute gradient of 1.5M NaCl in water. "NAP 5" columns from Pharmacia (Uppsala, Sweden) were used for desalting of oligonucleotides. Capillary electrophoresis (CE) analysis was performed on an ABI 270 A system with 10% MICROGEL™ capillaries (0.1×500 mm) in 35 mM Tris-borate buffer, pH 9.0. Thermal dissociation experiments were done on a Varian IE spectrophotometer and temperature controller. Absorbance values at 260 nm or 284 nm were obtained at 1 minute intervals at a heating rate of 1.0° C./minute.

EXAMPLE 1

SYNTHESIS OF OLIGONUCLEOTIDES CONTAINING OLIGODEOXYRIBONUCLEOTIDE N3'→P5' PHOSPHORAMIDATES

A. GENERAL METHODS.

Synthesis of the phosphoramidate analogs was carried out either manually in syringe or automatically on ABI 384 synthesizer (ABI, Foster City, Calif.).

FIG. 1E presents a schematic representation of the synthesis of uniformly modified oligonucleotides on a solid support using a step-by-step elongation procedure.

For a given cycle the chemical steps, reagents, and reaction times were (i) detritylation, 3% dichloroacetic acid in dichloromethane, 1.5 min. (FIG. 1, step i); (ii) phosphitylation, 0.2M 2-cyanoethyl-N,N-diisopropylchlorophospine and 0.2M diisopropylethylamine in dichloromethane, 10 min. (FIG. 1, steps ii); (iii) hydrolysis, 0.4M tetrazole in acetonitrile/water, 9/1 v/v, 5 min. (FIG. 1, step iii); (iv) coupling, 0.2M 5'-DMT-3'-amino nucleoside and 0.2M triethylamine in carbon tetrachloride/acetonitrile, 1/1, v/v, 20 min (FIG. 1, step iv).

Standard oligonucleotides have phosphodiester intersubunit linkages were synthesized by standard methods (ABI 384 synthesizer).

To construct chimeric oligomers, 5'-DMT-N-protected 3'-phosphoramidate dimer building blocks, having a 3'-NHP(O)(OCE)O-5' phosphoramidate internucleoside linkage group, were used for synthesis with the conventional phosphoramidate method (essentially as previously described by Gryaznov, et al., herein incorporated by reference).

Exemplary oligonucleotides synthesized by the method of the present invention are presented in FIG. 3. Further details of synthesis follow here.

B. MANUAL SYNTHESIS OF THE OLIGONUCLEOTIDE N3'→P5' PHOSPHORAMIDATES

Controlled pore glass (CPG) polymer support containing 1 μmol of 5'-DMT-N-protected nucleoside was placed in a 1 ml Hamilton gas tight syringe equipped with a plug of glass wool at the base.

For a given cycle of synthesis, reagents were drawn in and expelled from the syringe according to the following protocol:

1. Detritylation—3% dichloroacetic acid in dichloromethane, 5×0.5 ml: 1,5 min.
2. Washing—acetonitrile, 6×0.5 ml.
3. Phosphitilation—0.2M 2-cyanoethyl-N,N-diisopropylchlorophospine and 0.2M diisopropylethylamine in dichloromethane, 0.5 ml, 10 min with periodic shaking.
4. Hydrolysis—0.4M tetrazole in acetonitrile/water, 9/1, v/v, 5 minutes with periodic shaking.
5. Washing—anhydrous acetonitrile, 10×0.5 ml.
6. Coupling—0.2M 5'-DMT-3' amino nucleoside and 0.2M triethylamine in carbon tetrachloride/acetonitrile, 1/1, v/v, 20 minutes, with shaking. After coupling, the solution was collected to recover un-reacted nucleoside.
7. Washing—acetonitrile, 6×0.5 ml.

The steps 1–7 were repeated until the desired oligonucleotide was prepared. The average coupling yields were 94–96% as judged by DMT-cation assay. On completion of the cycles, the support-bound oligomer was detritylated. Cleavage from the support and N-deprotection with concentrated ammonium hydroxide afforded crude oligonucleotides which were purified by ion exchange HPLC.

C. MANUAL SYNTHESIS OF THE OLIGONUCLEOTIDE 2 CONTAINING ALTERNATIVE N3'→P5' PHOSPHORAMIDATE O3'→P5' PHOSPHODIESTER LINKAGES

5'-DMT-3'-amino thymidine and 5'-DMT-thymidine-3'-phosphoramidate subunits were used to synthesize oligonucleotides having alternative N3'→P5' phosphoramidate and O3'→P5' phosphodiester linkages For the synthesis of oligonucleotide 2 (SEQ ID NO:2), one micromole of T-CPG (Thymidine-linked-CPG) was placed in a 1 ml Hamilton gas tight syringe Addition of 5'-DMT-3'-amino thymidine subunits was carried out as described above. Addition of 5'-DMT-thymidine-3'-phosphoramidate subunits was carried out by standard synthetic procedures (Applied Biosystems, Foster City, Calif.).

After the 9th coupling reaction, the polymer support was treated with concentrated ammonia hydroxide to release the crude oligomer. The oligonucleotide was purified by ion exchange HPLC (e.g., Example 2). Oligonucleotide SEQ ID NO:2 was analyzed by CE and $^{31}$p NMR (e.g., Example 2).

D. SYNTHESIS OF THE 5'-DMT-N-ISOBUTYRYL-3'-AMINO-2',3'-DIDEOXYGUANOSINE

The following steps describe a method of synthesis of 5'-DMT-N-isobutyryl-3'-amino-2',3'-dideoxyguanosine.

1. 5'-O-BENZOYL-N-ISOBUTYRYL-2'-DEOXYGUANOSINE was prepared from N-isobutyryl-2'-deoxyguanosine essentially according to the method of Nishino, et al. (1986), except that the product was purified as follows: partitioning between $CH_2Cl_2$ and water, concentrating the CH2Cl$_2$ layer in vacuo, and crystallizing the product with ether. After recovery by filtration, the product was stirred overnight in fresh ether and recollected by filtration. The overall yield of 5'-O-benzoyl-N-isobutyryl-2'deoxyguanosine was 50–80%.

2. 5'-O-BENZOYL-N-ISOBUTYRYL-2'-DEOXYXYLOGUANOSINE was prepared from 5'-O-benzoyl-N-isobutyryl-2'-deoxyguanosine essentially according to the method of Herdewijn and van Aerschot (1989). The product was purified by drying the crude mixture in vacuo, then dissolving in $CH_2Cl_2$. The 3'-O-benzoyl-N-isobutyryl-2'-deoxyxloguanosine product spontaneously precipitated and was obtained by filtration.

3. 5'-O-(4,4'-DIMETHOXYTRITYL)-3'-O-BENZOYL-N-ISOBUTYRYL-2'-DEOXYXYLOGUANOSINE.
Dry 3'-O-benzoyl-N-isobutyryl-2'-deoxyxyloguanosine (7.3 g) and 7.9 g 4,4'-dimethoxytrityl chloride were dissolved in 150 mL anhydrous pyridine. After 24 hours, 1 mL of water was added to the mixture. The mixture was then concentrated in vacuo to a foam containing the 5'-O-(4,4'-dimethoxytrityl)-3'-O-benzoyl-N-isobutyryl-2-deoxyxyloguanosine product. The foam was dissolved in 300 mL $CH_2Cl_2$, washed with 250 mL water, and reconcentrated in vacuo.

4. 5'-O-(4,4'-DIMETHOXYTRITYL)-N-ISOBUTYRYL-2'-DEOXYXYLOGUANOSINE.

The crude 5'-O-(4,4'-dimethoxytrityl)-3'-O-benzoyl-N-isobutyryl-2'-deoxyxyloguanosine was dissolved in 1.2 L 5:4:1 dioxane:methanol:water and cooled in an ice bath. To this mixture, 120 mL 2N NaOH was added. The resulting mixture was stirred at 0° C. for 25 minutes, and neutralized with pyridinium $H^+$-form Dowex 50 ion exchange resin. After 2–3 minutes, the resin was removed by filtration and the product concentrated to a slurry in vacuo. The white precipitate in the slurry (5'-O-(4,4'-dimethoxytrityl)-N-isobutyryl-2-deoxyxyloguanosine) was removed by filtration, washed with water, air dried and desiccated under vacuum over $P_2O_5$.

5. 5'-O-(4,4'-DIMETHOXYTRITYL)-3-AMINO-N-ISOBUTYRYL-2', 3-DIDEOXYGUANOSINE.

To the crude 5'-O-(4,4'-dimethoxytrityl)-N-isobutyryl-2'-deoxyxyloguanosine, 7.9 g triphenylphosphine and 4.8 g $LiN_3$ were added. The mixture was further dried under vacuum over $P_2O_5$ for 3 hours. These dry compounds were dissolved in 450 mL anhydrous dimethylformamide. To this solution 5.3 mL diethyl azodicarboxylate was added. The mixture was stirred overnight, 1 mL water added, and the solvent removed in vacuo.

One liter $CH_2Cl_2$ was added to the dried mixture and the resulting mixture washed twice with 1 L of water each time. The $CH_2Cl_2$ layer was concentrated in vacuo to a light brown oil which was then dissolved in 600 mL 10% triethylamine in pyridine. This mixture was cooled in an ice bath and $H_2S$ added by bubbling. After 30 minutes, the ice bath was removed, and the $H_2S$ stream continued another 3 hours. The solution was concentrated in vacuo to a light brown oil.

Flash chromatography of the oil on a silica gel column, pretreated with 0.5% pyridine in $CH_2Cl_2$, then eluted with a gradient of 0–5% methanol in $CH_2Cl_2$ produced 3.5 g 5'-O-(4,4'-dimethoxytrityl)-3-amino-N-isobutyryl-2',3'-dideoxyguanosine (FIG. 1C).

E. SYNTHESIS OF THE 5'-DMT-N-BENZOYL-3'-AMINO-2', 3'-DIDEOXYADENOSINE

The steps of the synthesis of 3'-amino-$N^6$-5'-dimethoxytrityl-2', 3'-dideooxy-adenosine are illustrated in FIG. 20.

1. PREPARATION OF $N^6$ 5'-DIBENZOYL-2'-DEOXYADENOSINE.

A solution of benzoyl chloride (2.45 mL, 21 mmol) in pyridine (150 mL) was added drop-wise to a solution of N-benzoyl-2'-deoxyadenosine (compound 1, FIG. 20) (5 g, 14 mmol) in pyridine (45 mL) at room temperature over approximately 1 hour. The reaction mixture was stirred at room temperature for an additional hour. The reaction mixture was quenched with methanol (5 mL) and evaporated to dryness.

The residue was dissolved in $CH_2Cl_2$, washed with sat. aq. $NaHCO_3$ and $H_2O$. The organic layer was then dried over $Na_2SO_4$ and evaporated to dryness. This residue was dissolved in $CH_2Cl_2$ and subjected to column chromatography (silica gel, 70–230 mesh, 200 g), eluted with 5% $CH_3OH/CH_2Cl_2$, and the solvent removed by evaporation, yielding 6 g (93%) of the desired $N^6$5'-dibenzoyl-2'-deoxyadenosine product (compound 2, FIG. 20).

2. PREPARATION OF $N^6$-BENZOYL-9-(3-O-BENZOYL-2-DEOXY-β-THREO-PENTEOFURANOSYL) ADENINE.

Trifluoromethane sulfonic anhydride (4.2 mL, 25 mmol), was added to the suspension of $N^6$5'-dibenzoyl-2'-deoxyadenosine (7.5 g, 16.3 mmol) in 10% pyridine/$CH_2Cl_2$ (150 ML) at 0° C. The reaction was stirred at 0° C. for 30 minutes followed by the addition of $H_2O$ (26 mL). The reaction mixture was then stirred at room temperature overnight, and evaporated to dryness.

The residue was redissolved in $CH_2Cl_2$, washed with sat. aq. $NaHCO_2$, $H_2O$, and dried over $Na_2SO_4$. The organic layer was evaporated to dryness to give brown oil, containing the $N^6$-benzoyl-9-(3-O-benzoyl-2-deoxy-β-D-THREO-PENTEOFURANOSYL) ADENINE product (compound 3, FIG. 20), which was used without further purification.

3. PREPARATION OF $N^6$-BENZOYL-9-(3-O-BENZOYL-5-DIMETHOXYTRITYL-2-DEOXY-β-D-THREO-PENTOFURANOSYL) ADENINE. $N^6$-benzoyl-9-(3-O-benzoyl-2-deoxy-β-D-THREOPENTEOFURANOSYL) ADENINE was dissolved in pyridine (60 mL). Dimethozytrityl chloride was then stirred at room temperature overnight. The reaction was quenched with $CH_3OH$. The mixture was evaporated to dryness. The residue was redissolved in $CH_2Cl_2$, washed with sat. aq. $NaHCO_3$, $H_2O$, dried over $Na_2SO_4$ and evaporated. The residue was dissolved in $CH_2Cl_2$ and subjected to column chromatography (silica gel, 70–230 mesh, 400 g), eluted with 4% $CH_3OH/CH_2Cl_2$. The desired fraction containing the $N^6$-benzoyl-9-(3-O-benzoyl-5-dimethoxytrityl-2-deoxy-β-D-THREOPENTOFURANOSYL) ADENINE PRODUCT (COMPOUND 4, FIG. 20) was collected and evaporated to dryness. The yield of product was 7 g (56% from $N^6$5'-dibenzoyl-2'-deoxyadenosine).

4. PREPARATION OF $N^6$-BENZOYL-9-(5-O-DIMETHOXYTRITYL-2-DEOXY-β-D-THREO-PENTOFURANOSYL) ADENINE).

Aqueous NaOH (2 M, 40 mL) was added to a solution of $N^6$-benzoyl-9-(3-O-benzoyl-5-dimethoxytrityl-2-deoxy-β-D-THREO-PENTOFURANOSYL) ADENINE (7 g, 9.2 mmol) in a mixture of p-Dioxane (200 mL), $CH_3OH$ (160 ML) and $H_2O$ (40 mL) at 0° C. The reaction mixture was stirred at 0° C. for 25 minutes. The reaction was terminated by the addition of Dowex 50×2–100 ion-exchange resin (pyridinium form) to neutralize the solution to pH 7. The solid was removed by filtration and the solvent evaporated to dryness.

The residue was dissolved in $CH_2Cl_2$, washed with sat. aq. $NaHCO_3$, dried over $Na_2SO_4$ and evaporated to dryness to give light yellow solid containing the $N^6$-benzoyl-9-(5-O-dimethoxytrityl-2-deoxy-β-D-THREOPENTOFURANOSYL) ADENINE PRODUCT (COMPOUND 5, FIG. 20). This product was used without further purification. The yield of product from the previous step was 6 g (99%).

5. PREPARATION OF 3'-AMINO-$N^6$-BENZOYL-5'-DIMETHOXYTRITYL- 2',3'-DIDEOXY-ADENOSINE.

Diethylazodicarboxylate (1.42 mL, 9 mmol) was added to a suspension of $N^6$-benzoyl-9-(5-O-dimethoxytrityl-2-deoxy-β-D-THREO-PENTOFURANOSYL) ADENINE) (2 g, 3 mmol) in DMF (40 mL), the suspension further containing triphenylphosphine (2.4 g, 9 mmol) and $LiN_3$ (4.1 g, 83.8 mmol). The reaction mixture was stirred at room temperature overnight and evaporated to dryness. The residue was dissolved in $CH_2Cl_2$, washed with sat. aq. $NaHCO_3$, $H_2O$, dried over $Na_2SO_4$ and evaporated to give a brown oil. The brown oil was dissolved in $CH_2Cl_2$ and subjected to column chromatography (silica gel, 70–230 mesh, 100 g), eluted with 3% CH$_3$OH/CH$_2$Cl$_2$ to give compound 6 (FIG. 20) as light brown oil.

This oil was dissolved in 15% triethylamine/pyridine (36 mL). Hydrogen sulfide was then bubbled into the solution at 0° C. for 30 minutes. The solution was stirred at room temperature for 30 more minutes. The solvent was evaporated to dryness. The residue was dissolved in CH$_2$Cl$_2$, washed with sat. aq. NaHCO$_2$, H$_2$O, dried over NaSO$_4$ and evaporated to dryness. The residue was dissolved in CH$_2$Cl$_2$ and subjected to column chromatography (silica gel, 70–230 mesh, 100 g), eluted with 5% CH$_3$OH/CH$_2$Cl2 to give the final product 3'-amino-N$^6$-5'-dimethoxytrityl-2', 3'-dideooxy-adenosine (compound 7, FIG. 20; FIG. 1). The yield of the product from the previous step was 1.6 g (80%).

E. SYNTHESIS OF OTHER DMT-SUBUNITS

Synthesis of the 5'-DMT-3'amino thymidine and 5'-DMT-N-benzoyl-3'-amino cytidine was performed according to Glinski, et al. (1970).

EXAMPLE 2

CHARACTERIZATION OF OLIGONUCLEOTIDES CONTAINING N3'→P5' PHOSPHORAMIDATE LINKAGES

Oligonucleotides synthesized as described in Example 1 were evaluated by the following methods

A. PURIFICATION BY ION EXCHANGE CHROMATOGRAPHY

Oligonucleotides were purified away from excess reaction components by ion exchange (IE) HPLC. IE HPLC. analyses were performed on a Dionex (Sunnyvale, Calif.) chromatograph A Dionex "OMNIPAC. NA100, " 4×250 mm column was used, with a 1%/min or 2%/min gradient of 1.0 M NaCl in 0.03 M TEAA buffer, pH 7.0; flow rate, 1.0 ml/min.

FIG. 4A presents an exemplary HPLC chromatogram of the reaction mixture after synthesis of the phosphoramidate Oligonucleotide 3 (FIG. 3). The largest peak in the figure corresponds to the Oligonucleotide 3 product. Retention time of the 3'-NHP(O)(O$^-$)O-5' phosphoramidates on IE HPLC column was 1.0–1.5 minutes shorter than the retention time for corresponding phosphodiester compounds The product was then concentrated by precipitation with ethanol and resuspended in water.

B. PURITY OF OLIGONUCLEOTIDES

Purity of synthesized oligonucleotides was typically evaluated by capillary gel electrophoresis. Capillary electrophoresis was performed using an Applied Biosystems Incorporated Model 270A machine, on "MICKROGEL" capillary tubes, essentially following the directions of the manufacturer.

FIG. 4B presents an exemplary capillary gel electrophoresis profile of the reaction mixture after synthesis of the undecaphosphoramidate 6 (FIG. 3).

Alternatively, purity of the isolated oligonucleotides is evaluated by electrophoretic separation of the samples in high percent polyacrylamide gels, for example, 20% acrylamide, 5% bis-acrylamide (Ausubel, et al.; Maniatis, et al.). Oligonucleotides were visualized by staining with ethidium bromide and exposure to UV light. Relative mobilities in polyacrylamide gels upon electrophoretic separation of the 3'-NHP(O)(O$^-$)O-5' phosphoramidates was 10–15% lower than for the corresponding phosphodiester compounds.

C. NUCLEAR MAGNETIC RESONANCE ANALYSIS

NMR spectra were recorded on a Varian XL-400 (Varian Associates, Palo Alto, Calif.) spectrometer at 162 MHz for $^{31}$p spectra, with 85% phosphoric acid in D$_2$O as an external standard, and at 400 MHz for $^1$H spectra, with tetramethyl silane (TMS) as an external standard.

Exemplary results are presented in FIG. 4C, showing the $^{31}$P-NMR spectrum of the purified decaphosphoramidate oligonucleotide 3 (FIG. 3). The spectrum presents a peak at δ, ppm, 7.12 which is characteristic of phosphoramidate groups.

REVERSED PHASE HIGH PERFORMANCE LIQUID CHROMATOGRAPHY ANALYSIS OF HYDROLYSIS PRODUCTS

Purified phosphoramidate 10-mer oligonucleotide 3 (FIG. 3) was hydrolysed by treatment with 80% acetic acid for 48 hours at 25° C. The hydrolysis products were evaluated by reverse phased (RP) HPLC. RP HPLC analyses were performed with a Dionex chromatograph on a "HYPERSIL ODS" 5 μ, 4.6×200 mm column from Hewlett Packard (Palo Alto, Calif.), using a 1% min gradient of acetonitrile in 0.03 M TEAA buffer, pH 7.0; flow rate, 1 ml/min. The hydrolysis products were identified as 3' amino-5'-thymidilic acid, 5'-thymidilic acid, and 3'-aminothymidine. Further, about 7% of the hydrolysis products (total peaks) were minor by-products. These results confirm the presence of N3'→P5' phosphoramidate linkages in the oligonucleotide.

EXAMPLE 3

THERMAL DISSOCIATION

A. DUPLEX MELTING

Thermal dissociation curves were obtained using a Carry 1E spectrophotometer (Varian, Palo Alto, Calif.) that was equipped with a temperature controller (Varian). The reaction solutions contained equivalent concentrations of oligomer and complement (approximately 6 μM in oligomer strand) in 15 mM phosphate buffer at pH 7.05, with NaCl added to give a total Na+ concentration of 100 mM.

The molar extinction coefficients used for oligo(dT), poly(dA) and poly(A) were 8.2, 8.4, and 10.2 A$_{260}$ X 103, respectively. An extinction coefficient of 109 A$_{260}$ Units/μM was used for the mixed-based oligomers—the extinction coefficient was calculated from the table compiled by P. N. Borer (1975).

Reaction solutions were equilibrated at 0° C. and the absorbance at 260 nm was followed as the temperature was increased in increments of 3° C. per 5 minutes. The fraction of an oligomer in the bound state, α, at a given temperature was determined by use of upper and lower base lines as described by Abergo, et al. (1981). T$_m$ values are defined as the temperature at which α=0.5. Plots of lnk (Marky, et al., 1987) versus 1/T were linear for these compounds.

The results of the thermal denaturation studies were also plotted as normalized absorbance at 260 nm versus temperature in 0° C. FIGS. 5A and 5B display exemplary melting curves for the duplexes formed by phosphodiester and phosphoramidate oligomers. In the figures: (A),(C) and (B),(D), respectively, correspond to FIG. 3, experiments 8, 9, using phosphodiester Oligonucleotide SEQ ID NO:4); and, FIG. 3, experiments 13, 14 using phosphoramidate Oligonucleotide SEQ ID NO:6).

The thermal stability data is summarized in FIG. 3 {T$_m$(° C.)}. In the table, T$_m$ is the temperature at the midpoint of the melting curve; np is the abbreviation for the 3'-NHP(O)(O$^-$)O-5' phosphoramidate link.

The concentrations of oligonucleotides were typically at 5 µM oligomer strands. Buffer A (10 mM Tris HCl, 150 mM NaCl, pH 7.02) was used for duplex thermal stability studies.

B. OLIGONUCLEOTIDE HAIRPINS

The stability of duplexes formed by oligonucleotides containing phosphoramidate linkages in both complementary strands was evaluated essentially as described above. The chimeric phosphoramidate-phosphodiester hairpin oligomers presented in FIG. 6 were synthesized.

All the molecules in FIG. 6 were constructed using 2'-deoxyribonucleotides.

Thermal dissociation experiments were performed essentially as described above, but with the following reaction conditions: 10 mM Tris HCl buffer, pH 7.02 at oligonucleotide concentration 2.5 µM.

The $T_m$ values obtained from these experiments are summarized in FIG. 6.

C. TRIPLEX MELTING

Triplex thermal stabilities were evaluated essentially as described above for duplexes. Buffer conditions were either as described above (Buffer A) or a second buffer, Buffer B (10 mM Tris HCl, 150 mM NaCl, 10 mM $MgCl_2$, pH 7.02.) was used.

Figure 7A:
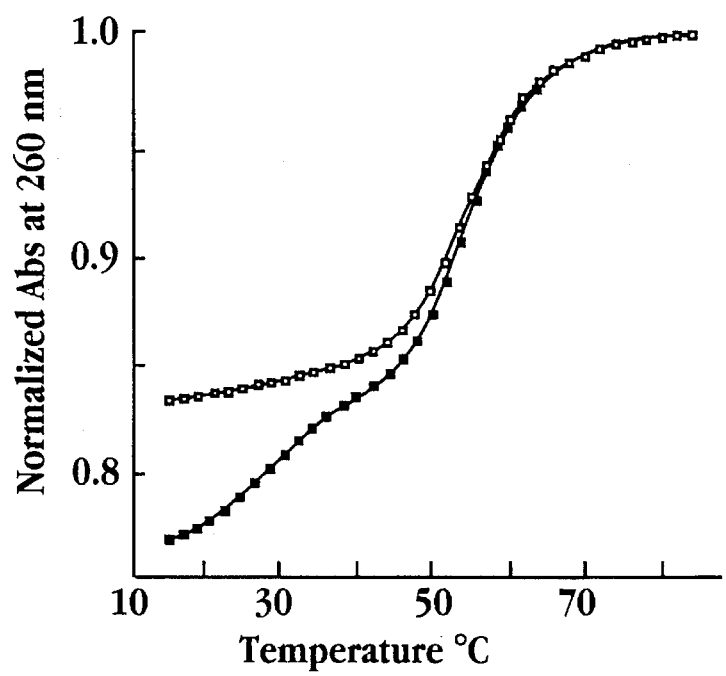
Figure 7B:
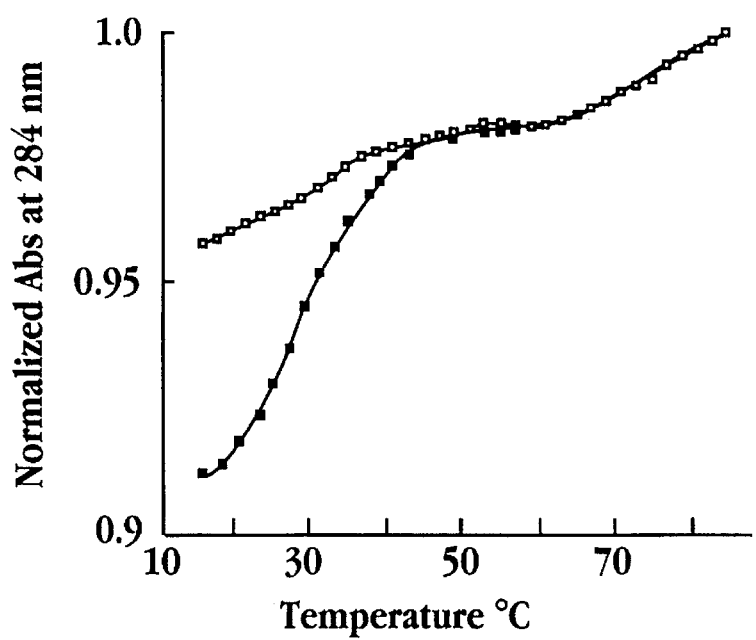
Figure 7C:
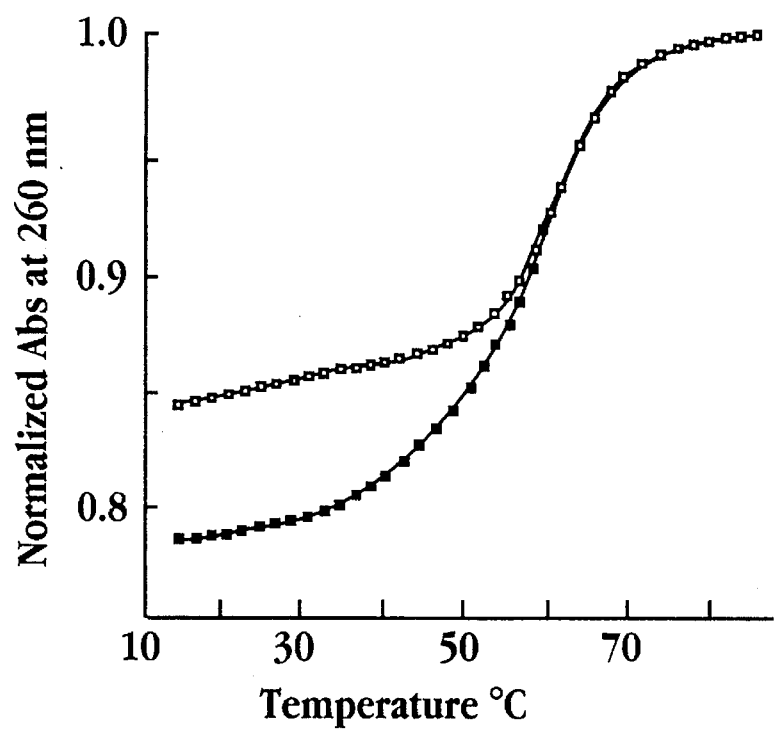
Figure 7D:
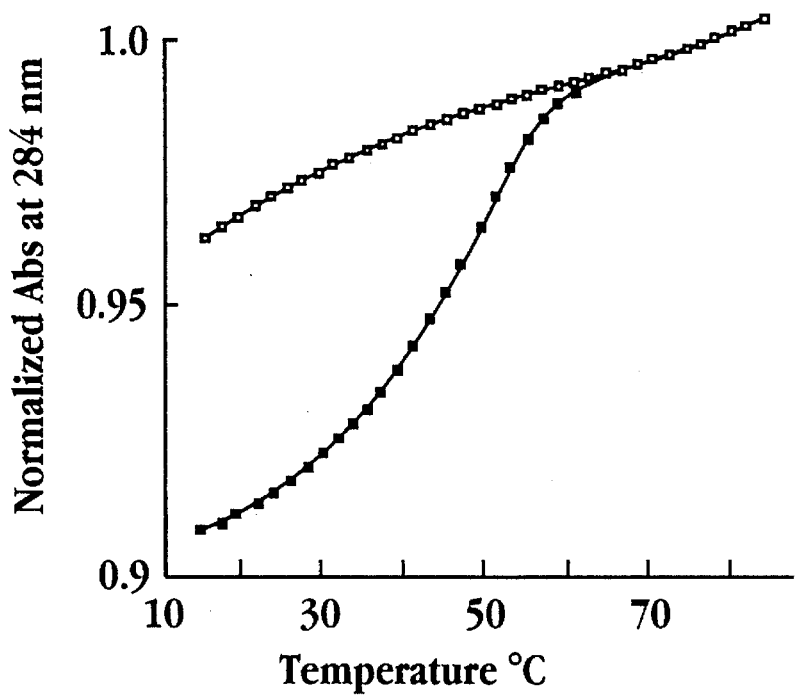

FIGS. 7A to 7D present exemplary triplex melting curves. FIGS. 7A and 7C present normalized absorbance at 260 nm plotted against temperature. FIGS. 7B and 7D present normalized absorbance at 284 nm plotted against temperature. In the figures: the triplexes formed by double stranded DNA and phosphoramidate Oligonucleotide SEQ ID NO:3 correspond to the black circle line; triplexes formed with phosphodiester Oligonucleotide SEQ ID NO:1 correspond to open squares line).

The data correspond to FIG. 3, experiment 7 where curves (A) and (C) were thermal stability studies performed using buffers A and B, respectively, with hyperchromicity monitored at 260 nm. Curves (B) and (D) are (A) and (C) respectively, but where hyperchromicity was monitored at 284 nm.

The data presented in FIGS. 7A to 7D indicate that phosphodiester Oligonucleotide SEQ ID NO:1 did not form triplexes with the same double-stranded DNA targets as did phosphoramidate Oligonucleotide SEQ ID NO:3.

EXAMPLE 4

GEL BAND MOBILITY SHIFT ASSAYS

Triplex structures were further evaluated using gel band mobility shift assays.

A. PHOSPHORAMIDATE OLIGONUCLEOTIDE SEQ ID NO:3

Gel band mobility shift assay conditions were as follows: 20% acrylamide, 5% bis-acrylamide in 10 mM $MgCl_2$, 80 mM Tris-borate buffer, pH 8.2, 10° C. Gels were typically run under native (non-denaturing) conditions. Exemplary results of such a gel band mobility shift assay are presented in FIG. 8. In the figure the lanes are as follows: 1–10—mer phosphodiester Oligonucleotide SEQ ID NO:1; 2–10—mer phosphoramidate Oligonucleotide SEQ ID NO:3; 3–24—mer hairpin target $d(A_{10}C_4T_{10})$ (FIG. 3, experiment 7). In lane 3 the slow moving minor band likely corresponds to a bi-molecular duplex of $d(A_{10}C_4T_{10})$; 4—hairpin target and Oligonucleotide SEQ ID NO:1; 5—hairpin target and Oligonucleotide SEQ ID NO:3.

The gel was stained with STAINS-ALL™ (Kodak, Rochester, N.Y.) and imaged on a Molecular Dynamics (Sunnyvale, Calif.) densitometer. The efficiency of the phosphoramidate Oligonucleotide SEQ ID NO:3 staining is different from phosphodiester compounds (Oligonucleotide SEQ ID NO:1 and the duplex).

In the figure the mobility of the triplex structure is denoted by arrow. As can be seen from the results presented in the figure, the gel band mobility shift assay results confirm the results obtained from thermal denaturation studies, i.e., that Oligonucleotide SEQ ID NO:4 fails to form a triplex with the same target as Oligonucleotide SEQ ID NO:3.

B. PHOSPHORAMIDATE OLIGONUCLEOTIDE SEQ ID NO:6

The triplex formation of phosphoramidate Oligonucleotide SEQ ID NO:6 analog with a double-stranded DNA target was also confirmed by gel band mobility shift assay.

The conditions of the gel band mobility shift assay were essentially as described above. The results of the analyses are presented in FIG. 9. In the figure the lanes were as follows: 1–11—mer phosphodiester Oligonucleotide SEQ ID NO:4; 2–11—mer phosphoramidate Oligonucleotide SEQ ID NO:6; 3–26—mer hairpin target (SEQ ID NO:22); 4—hairpin target and Oligonucleotide SEQ ID NO:4; 5—hairpin target and Oligonucleotide SEQ ID NO:6.

In the figure the mobility of the triplex structure is denoted by arrow. As seen above, the phosphodiester Oligonucleotide SEQ ID NO:4 fails to form a triplex with the same target as Oligonucleotide SEQ ID NO:6.

EXAMPLE 5

IN VITRO EVALUATION OF PHOSPHORAMIDATE ANALOGS

N3'→P5' phosphoramidate linkage containing antisense oligonucleotides were synthesized which were complementary to the BCR/ABL fusion junction (B2A2) in leukemic cell line BV173. The following assay measures leukemic cell proliferation and is performed essentially as described by Anfossi, et al. (1989).

Briefly, FIG. 10 illustrates the effect of BCR-ABL oligomers on leukemic cell proliferation of BV173 cells carrying the B2A2-type break points. BV173 is a leukemic cell line with the B2A2 BCR/ABL fusion junction (Pegoraro, et al., 1983). HL60 is a promyelocytic leukemic cell line with a normal c-abl locus (Collins, et al., 1977). K562 is a leukemic cell line with the B3A2 BCR/ABL fusion junction (Seelig, et al., 1993).

Cells (5×104) were placed in 0.2 ml of liquid suspension culture (Iscove's modified Dulbecco's modified medium with 2% human AB serum—Life Technologies, Gaithersburg, Md.).

The oligonucleotides were administered to the cultures at 24 hour intervals for three days (days 0, 1 and 2) to achieve the incremental concentrations shown in the legends of FIGS. 10–19 (all concentrations in µg/mL), for example, FIG. 10—40/20/20; 20/10/10; 10/5/5; and 5/2.5/2.5. Note that, for example, 40/20/20 reflects a final total concentration of 80 µg/ml in the cell culture medium after the last oligonucleotide addition. Cell counts were performed by standard methods.

FIG. 10 shows the results of the assay using fully modified N3'→P5' phosphoramidate oligonucleotide 6 (SEQ ID NO:6) at the concentrations shown in the figure legend. The target cells were BV173 cells. The results demonstrate that the phosphoramidate oligonucleotide is extremely effective at inhibiting the growth of the leukemia cells—even at the lowest concentration used.

FIG. 11 shows the results of treatment of the HL60 cells, a non-BRC-ABL expressing cell line, with oligonucleotide SEQ ID NO:6. The results demonstrate that at all concentrations the oligonucleotide was well tolerated by the cells. There was no apparent cytotoxicity.

FIGS. 12 and 13 show the results of similar experiments to the results presented in FIGS. 10 and 11, respectively. Even at the lowest concentrations (0.3125/0.15625/0.15625) the N3'→P5' phosphoramidate oligonucleotide SEQ ID NO:6 is extremely effective at inhibiting leukemia cell proliferation (FIG. 12) while maintaining negligible toxicity (FIG. 13).

FIGS. 14 and 15 show the results of similar experiments to the results presented in FIGS. 10 and 11, respectively. However, in the experiment corresponding to the data presented in FIG. 15 the target cell was K562, which contains a B3A2 BCR/ABL fusion junction. In the data from the experiment presented in FIG. 14, transition concentrations for the effectiveness of the N3'→P5' phosphoramidate oligonucleotide SEQ ID NO:6 in culture are shown. Specifically, at a concentration of 0.0198/0.0098/0.0098 some release of inhibition of proliferation can be seen with oligonucleotide SEQ ID NO:6.

Further, the data presented in FIG. 15 demonstrate that phosphoramidate oligonucleotide SEQ ID NO:6 had essentially no effect on the proliferation of K562 cells, having the B3A2 fusion junction. These results demonstrate that the antiproliferation effect is specifically associated with the B2A2 BCR/ABL fusion junction to which phosphoramidate oligonucleotide SEQ ID NO:6 is complementary.

In comparison, FIGS. 16–19 present similar data for a 16-mer (SEQ ID NO:26) having fully modified phosphorothioate intersubunit linkages.

FIG. 16 shows the results of the assay using fully modified phosphorothioate 16-mer (SEQ ID NO:26) at the concentrations shown in the figure legend where the target cell line was BV173. The results are similar to those seen with oligonucleotide SEQ ID NO:6 (FIG. 10), but the data demonstrate that the phosphorothioate oligonucleotide is not as effective as oligonucleotide SEQ ID NO:6 at inhibiting the growth of the leukemia cells.

FIG. 17 shows the results of treatment of the BV173 BRC/ABL cell line with a 16-mer phosphorothioate oligonucleotide (SEQ ID NO:27) having a sequence complementary to the B3A2 BCR/ABL fusion junction: B3A2 has a 2 base pair sequence mismatch to the B2A2 BCR/ABL fusion junction. The results demonstrate that at all concentrations the oligonucleotide was tolerated by the cells.

Figure 19:
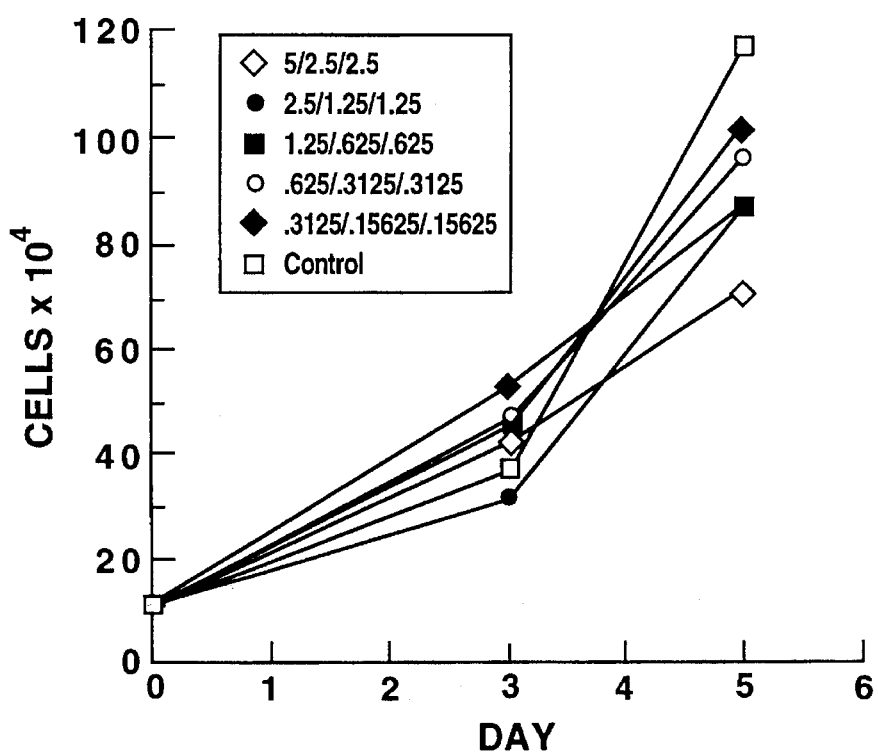

FIGS. 18 and 19 show the results of similar experiments to the results presented in FIGS. 16 and 17, respectively. In the data from these experiments, the release of the inhibition of cellular proliferation is seen at much lower concentrations for the phosphorothioate oligonucleotide than was seen for the N3'→P5' phosphoramidate oligonucleotide SEQ ID NO:6.

These results demonstrate the in vitro N3'→P5' phosphoramidate oligonucleotides are effective antisense compounds at low concentrations. Further, the N3'→P5' phosphoramidate oligonucleotides are better antisense agents than phosphorothioate oligonucleotides.

While the invention has been described with reference to specific methods and embodiments, it will be appreciated that various modifications and changes may be made without departing from the invention.

---

It is claimed:

1. A method of enhancing resistance of an oligodeoxyribonucleotide to snake venom phosphodiesterase, comprising:

forming an oligodeoxyribonucleotide having at least 9 inter-subunit linkages, wherein at least 50% of said inter-subunit linkages are N3'→P5' phosphoramidate inter-subunit linkages of the formula:

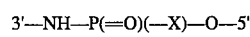

where X is O⁻ or —OR, and R is a 1 to 5 carbon alkyl, wherein said oligodeoxyribonucleotide is more resistant to snake venom phosphodiestrase digestion than a corresponding oligodeoxyribonucleotide having only phosphodiester inter-subunit linkages.

2. The method of claim 1, wherein all of said inter-subunit linkages of said oligodeoxyfibonucleotide are N3'→N5' phosphorsinitiate linkages.

3. The method of claim 2, wherein said oligodeoxyribonuclcotide has 10 to 50 nucleosides.

4. The method of claim 1, wherein said inter-subunit linkages alternate between N3'→P5' phosphormidate linkages and phosphodiester linkages.

5. The method of claim 4, wherein said oligodeoxyribonucleotide has 10 to 50 nucleosides.

6. The method of claim 1, wherein said oligodeoxyribonucleotide has 10 to 24 nucleosides.

7. The method of claim 1, wherein said N3'→P5' phosphoramidatc inter-subunit linkages are of the formula:

$$3'—NH—P(=O)(—X)—O—5'$$

where X is O⁻, methoxy or ethoxy and said oligodeoxyribonucleotide has 10 to 50 nucleosides.

8. The method of claim 7 wherein all of said inter-subunit linkages of said oligodeoxyribonucleotide are N3'→N5' phosphorsinitiate linkages.

9. The method of claim 7, wherein said inter-subunit linkages alternate between N3'→P5' phosphoramidate linkages and phosphodiester linkages.

10. The method of claim 7, wherein X is O⁻.

11. The method of claim 9, wherein said oligodeoxyribonucleotide has 10 to 24 nucleosides.

12. The method of claim 7, wherein said oligodeoxyribonucleotide hybridizes to mRNA from a proto-oncogene.

13. The method of claim 12, wherein said mRNA is from c-myc.

14. The method of claim 12, wherein said mRNA is from c-fos.

15. The method of claim 7, wherein said oligodeoxyribonucleotide hybridizes to RNA or a polynucleotide that is complementary to said RNA, wherein said RNA is derived from an organism selected from the group consisting of a virus, a bacteria, and a fungus.

16. The method of claim 15, wherein said virus is HIV, papillomavirus, or herpes virus.

17. The method of claim 7, wherein said oligodeoxyribonucleotide hydrizes to a single-stranded DNA target.

18. A method of enhancing resistance of an oligodeoxyribonucleotide to snake whom phosphodiesterase, comprising:

forming an oligodeoxyribonucleotide having inter-subunit linkages and 11 to 50 nucleosides, wherein at least 50% of said inter-subunit linkages are N3'→P5' phosphoramidate inter-subunit linkages of the formula:

$$3'—NH—P(=O)(—X)—O—5'$$

where X is O⁻ or —OR, and R is a 1 to 5 carbon all, wherein said oligodeoxyfibonucleotide is more resistant to snake venom phosphodiesterase digestion than a corresponding oligodeoxyfibonucleotide having only phosphodiester inter-subunit linkages.

19. The method of claim 18, wherein X is O⁻ and said oligodeoxyribonucleotide has 11 to 24 nucleosides.

20. The method of claim 18, wherein said snake venom phosphodiesterase is from Crotalus durissus.

21. The method of claim 18, wherein said inter-subunit linkages alternate between N3'→P5' phosphoramidate linkages and phosphodiester linkages.

22. The method of claim 21, wherein said oligodeoxyribonucleotide has 11 to 24 nucleotides.

23. The method of claim 18, wherein said oligodeoxyribonucleotide has 11 to 24 nucleosides.

24. The method of claim 18, wherein said oligodeoxyribonucleotide carries a reporter moiety.

25. The method of claim 24, wherein said reporter moiety is selected from the group consisting of radioactive labels, biotin labels, and fluorescent labels.

26. A method of enhancing resistance of an oligodeoxyfibonucleotide to snake venom phosphodiesterase, comprising:

forming an oligodeoxyribonucleotide comprising a defined sequence of nucleoside subunits joined by inter-subunit linkages and defined by the formula:

wherein B is a purine or pyrimidine or an analog thereof and n is between 4 and 50, wherein said oligodeoxyribonucleotide is more resistant to snake venom phosphodiesterase digestion than a corresponding oligodeoxyribonucleotide having only phosphodiester inter-subunit linkages.

27. The method of claim 26, wherein B of said oligonucleotide is selected from the group consisting of uracil, thymine, adenine, guanine, cytosine, 5-methylcytosine, 5-bromouracil, arid inosine.

28. The method of claim 27, wherein B of said oligonucleotide is selected from the group consisting of uracil, thymine, adenine, guanine, and cytosine.

29. The method of claim 28, wherein said oligodeoxyribonucleotide hybridizes to a nuleic acid target sequence.

30. The method of claim 29, wherein said oligodeoxyfibonucleotide hybridizes to an RNA target.

31. The method of claim 30, wherein said oligodeoxyribonucleotide carries a reporter moiety.

32. The method of claim 31, wherein said reporter moiety is selected from the group consisting of radioactive labels, biotin labels, and fluorescent labels.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA Oligonucleotide 1, FIG. 2

( x i ) SEQUENCE DESCRIPTION: SEQ ID NO:1:

T T T T T T T T T T                 1 0

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DNA Oligonucleotide 2, FIG. 2

(ix) FEATURE:
        (A) NAME/KEY: misc_feature
        (B) LOCATION: 1..2
        (D) OTHER INFORMATION: /note="where the intersubunit bond is 'np'"

(ix) FEATURE:
        (A) NAME/KEY: misc_feature
        (B) LOCATION: 3..4
        (D) OTHER INFORMATION: /note="where the intersubunit bond is 'np'"

(ix) FEATURE:
        (A) NAME/KEY: misc_feature
        (B) LOCATION: 5..6
        (D) OTHER INFORMATION: /note="where the intersubunit bond is 'np'"

(ix) FEATURE:
        (A) NAME/KEY: misc_feature
        (B) LOCATION: 7..8
        (D) OTHER INFORMATION: /note="where the intersubunit bond is 'np'"

(ix) FEATURE:
        (A) NAME/KEY: misc_feature
        (B) LOCATION: 9..10
        (D) OTHER INFORMATION: /note="where the intersubunit bond is 'np'"

(xi) SEQUENCE DESCRIPTION: SEQ ID NO:2:

TTTTTTTTTT                                                                                          10

(2) INFORMATION FOR SEQ ID NO:3:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DNA Oligonucleotide 3, FIG. 2

(ix) FEATURE:
        (A) NAME/KEY: misc_feature
        (B) LOCATION: 1..11
        (D) OTHER INFORMATION: /note="where the intersubunit bonds are 'np'"

(xi) SEQUENCE DESCRIPTION: SEQ ID NO:3:

TTTTTTTTTT T                                                                                        11

(2) INFORMATION FOR SEQ ID NO:4:

(i) SEQUENCE CHARACTERISTICS:
        (A) LENGTH: 11 base pairs
        (B) TYPE: nucleic acid
        (C) STRANDEDNESS: single (D) TOPOLOGY: linear (ii) MOLECULE TYPE: DNA (iii) HYPOTHETICAL: NO (iv) ANTI-SENSE: NO (vi) ORIGINAL SOURCE:
    (C) INDIVIDUAL ISOLATE: DNA Oligonucleotide 4, FIG. 2

(xi) SEQUENCE DESCRIPTION: SEQ ID NO:4:

CTTCTTCCTT A          11

(2) INFORMATION FOR SEQ ID NO:5:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (vi) ORIGINAL SOURCE:
        (C) INDIVIDUAL ISOLATE: RNA Oligonucleotide 5, FIG. 2

(xi) SEQUENCE DESCRIPTION: SEQ ID NO:5:

CTTCTTCCTT A          11

(2) INFORMATION FOR SEQ ID NO:6:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DNA Oligonucleotide 6, FIG. 2

(ix) FEATURE:
        (A) NAME/KEY: misc_feature
        (B) LOCATION: 1..11
        (D) OTHER INFORMATION: /note="where the intersubunit
            bonds are "np'""

(xi) SEQUENCE DESCRIPTION: SEQ ID NO:6:

CTTCTTCCTT A          11

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO ( v i ) ORIGINAL SOURCE:
   ( C ) INDIVIDUAL ISOLATE: DNA Oligonucleotide 7, FIG. 5

( x i ) SEQUENCE DESCRIPTION: SEQ ID NO:7:

TATATATATA TTTTTATATA TATA                                                                      24

( 2 ) INFORMATION FOR SEQ ID NO:8:

( i ) SEQUENCE CHARACTERISTICS:
      ( A ) LENGTH: 20 base pairs
      ( B ) TYPE: nucleic acid
      ( C ) STRANDEDNESS: both
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: DNA Oligonucleotide 8, FIG. 5

( i x ) FEATURE:
      ( A ) NAME/KEY: misc_feature
      ( B ) LOCATION: 1..2
      ( D ) OTHER INFORMATION: /note="where the intersubunit bond
         is "np'""

( i x ) FEATURE:
      ( A ) NAME/KEY: misc_feature
      ( B ) LOCATION: 3..4
      ( D ) OTHER INFORMATION: /note="where the intersubunit bond
         is "np'""

( i x ) FEATURE:
      ( A ) NAME/KEY: misc_feature
      ( B ) LOCATION: 5..6
      ( D ) OTHER INFORMATION: /note="where the intersubunit bond
         is "np'""

( i x ) FEATURE:
      ( A ) NAME/KEY: misc_feature
      ( B ) LOCATION: 7..8
      ( D ) OTHER INFORMATION: /note="where the intersubunit bond
         is "np'""

( x i ) SEQUENCE DESCRIPTION: SEQ ID NO:8:

TATATATATT TTTATATATA                                                                           20

( 2 ) INFORMATION FOR SEQ ID NO:9:

( i ) SEQUENCE CHARACTERISTICS:
      ( A ) LENGTH: 24 base pairs
      ( B ) TYPE: nucleic acid
      ( C ) STRANDEDNESS: both
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: DNA Oligonucleotide 9, FIG. 5

( i x ) FEATURE:
      ( A ) NAME/KEY: misc_feature
      ( B ) LOCATION: 1..2
      ( D ) OTHER INFORMATION: /note="where the intersubunit bond
         is "np'""

( i x ) FEATURE:
      ( A ) NAME/KEY: misc_feature
      ( B ) LOCATION: 3..4

(D) OTHER INFORMATION: /note="where the intersubunit bond is "np""

(ix) FEATURE:
    (A) NAME/KEY: misc_feature
    (B) LOCATION: 5..6
    (D) OTHER INFORMATION: /note="where the intersubunit bond is "np""

(ix) FEATURE:
    (A) NAME/KEY: misc_feature
    (B) LOCATION: 7..8
    (D) OTHER INFORMATION: /note="where the intersubunit bond is "np""

(ix) FEATURE:
    (A) NAME/KEY: misc_feature
    (B) LOCATION: 9..10
    (D) OTHER INFORMATION: /note="where the intersubunit bond is "np""

(ix) FEATURE:
    (A) NAME/KEY: misc_feature
    (B) LOCATION: 15..16
    (D) OTHER INFORMATION: /note="where the intersubunit bond is "np""

(ix) FEATURE:
    (A) NAME/KEY: misc_feature
    (B) LOCATION: 17..18
    (D) OTHER INFORMATION: /note="where the intersubunit bond is "np""

(ix) FEATURE:
    (A) NAME/KEY: misc_feature
    (B) LOCATION: 19..20
    (D) OTHER INFORMATION: /note="where the intersubunit bond is "np""

(ix) FEATURE:
    (A) NAME/KEY: misc_feature
    (B) LOCATION: 21..22
    (D) OTHER INFORMATION: /note="where the intersubunit bond is "np""

(ix) FEATURE:
    (A) NAME/KEY: misc_feature
    (B) LOCATION: 23..24
    (D) OTHER INFORMATION: /note="where the intersubunit bond is "np""

(xi) SEQUENCE DESCRIPTION: SEQ ID NO:9:

TATATATATA TTTTTATATA TATA          24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DNA Oligonucleotide 10, FIG. 5

(xi) SEQUENCE DESCRIPTION: SEQ ID NO:10:

TACGTACGTA TTTTTACGTA CGAT          24

(2) INFORMATION FOR SEQ ID NO:11:

( i ) SEQUENCE CHARACTERISTICS:
    ( A ) LENGTH: 24 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DNA Oligonucleotide 11, FIG. 5

( i x ) FEATURE:
    ( A ) NAME/KEY: misc_feature
    ( B ) LOCATION: 1..2
    ( D ) OTHER INFORMATION: /note="where the intersubunit bond is "np""

( i x ) FEATURE:
    ( A ) NAME/KEY: misc_feature
    ( B ) LOCATION: 3..4
    ( D ) OTHER INFORMATION: /note="where the intersubunit bond is "np""

( i x ) FEATURE:
    ( A ) NAME/KEY: misc_feature
    ( B ) LOCATION: 5..6
    ( D ) OTHER INFORMATION: /note="where the intersubunit bond is "np""

( i x ) FEATURE:
    ( A ) NAME/KEY: misc_feature
    ( B ) LOCATION: 7..8
    ( D ) OTHER INFORMATION: /note="where the intersubunit bond is "np""

( i x ) FEATURE:
    ( A ) NAME/KEY: misc_feature
    ( B ) LOCATION: 9..10
    ( D ) OTHER INFORMATION: /note="where the intersubunit bond is "np""

( x i ) SEQUENCE DESCRIPTION: SEQ ID NO:11:

TACGTACGTA TTTTTACGTA CGTA    24

( 2 ) INFORMATION FOR SEQ ID NO:12:

( i ) SEQUENCE CHARACTERISTICS:
    ( A ) LENGTH: 24 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DNA Oligonucleotide 12, FIG. 5

( i x ) FEATURE:
    ( A ) NAME/KEY: misc_feature
    ( B ) LOCATION: 1..2
    ( D ) OTHER INFORMATION: /note="where the intersubunit bond is "np""

( i x ) FEATURE:
    ( A ) NAME/KEY: misc_feature
    ( B ) LOCATION: 3..4
    ( D ) OTHER INFORMATION: /note="where the intersubunit bond is "np""

( i x ) FEATURE:

(A) NAME/KEY: misc_feature
                (B) LOCATION: 5..6
                (D) OTHER INFORMATION: /note="where the intersubunit bond
                    is "np""

(ix) FEATURE:
                (A) NAME/KEY: misc_feature
                (B) LOCATION: 7..8
                (D) OTHER INFORMATION: /note="where the intersubunit bond
                    is "np""

(ix) FEATURE:
                (A) NAME/KEY: misc_feature
                (B) LOCATION: 9..10
                (D) OTHER INFORMATION: /note="where the intersubunit bond
                    is "np""

(ix) FEATURE:
                (A) NAME/KEY: misc_feature
                (B) LOCATION: 15..16
                (D) OTHER INFORMATION: /note="where the intersubunit bond
                    is "np""

(ix) FEATURE:
                (A) NAME/KEY: misc_feature
                (B) LOCATION: 17..18
                (D) OTHER INFORMATION: /note="where the intersubunit bond
                    is "np""

(ix) FEATURE:
                (A) NAME/KEY: misc_feature
                (B) LOCATION: 19..20
                (D) OTHER INFORMATION: /note="where the intersubunit bond
                    is "np""

(ix) FEATURE:
                (A) NAME/KEY: misc_feature
                (B) LOCATION: 21..22
                (D) OTHER INFORMATION: /note="where the intersubunit bond
                    is "np""

(ix) FEATURE:
                (A) NAME/KEY: misc_feature
                (B) LOCATION: 23..24
                (D) OTHER INFORMATION: /note="where the intersubunit bond
                    is "np""

(xi) SEQUENCE DESCRIPTION: SEQ ID NO:12:

TACGTACGTA TTTTTACGTA CGTA                                                                      24

(2) INFORMATION FOR SEQ ID NO:13:

(i) SEQUENCE CHARACTERISTICS:
                (A) LENGTH: 24 base pairs
                (B) TYPE: nucleic acid
                (C) STRANDEDNESS: both
                (D) TOPOLOGY: linear (ii) MOLECULE TYPE: DNA (iii) HYPOTHETICAL: NO (iv) ANTI-SENSE: NO (vi) ORIGINAL SOURCE:
                (C) INDIVIDUAL ISOLATE: DNA Target, Experiment 7, FIG. 2

(xi) SEQUENCE DESCRIPTION: SEQ ID NO:13:

AAAAAAAAAA CCCCTTTTTT TTTT                                                                      24

(2) INFORMATION FOR SEQ ID NO:14:

(i) SEQUENCE CHARACTERISTICS:
                (A) LENGTH: 13 base pairs
                (B) TYPE: nucleic acid
                (C) STRANDEDNESS: single (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DNA Target, Experiment 8, FIG. 2

(xi) SEQUENCE DESCRIPTION: SEQ ID NO:14:

ATAAGGAAGA AGC 13

(2) INFORMATION FOR SEQ ID NO:15:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (vi) ORIGINAL SOURCE:
        (C) INDIVIDUAL ISOLATE: RNA Target, Experiment 9, FIG. 2

(xi) SEQUENCE DESCRIPTION: SEQ ID NO:15:

AUAAGGAAGA AGC 13

(2) INFORMATION FOR SEQ ID NO:16:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (vi) ORIGINAL SOURCE:
        (C) INDIVIDUAL ISOLATE: RNA Target, Experiment 10, FIG. 2

(xi) SEQUENCE DESCRIPTION: SEQ ID NO:16:

AUAAGGUAGA AGC 13

(2) INFORMATION FOR SEQ ID NO:17:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (vi) ORIGINAL SOURCE:
        (C) INDIVIDUAL ISOLATE: RNA Target, Experiment 11, FIG. 2

(xi) SEQUENCE DESCRIPTION: SEQ ID NO:17:

AUAAGGAAGA AGC 13

( 2 ) INFORMATION FOR SEQ ID NO:18:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( v i ) ORIGINAL SOURCE:
        ( C ) INDIVIDUAL ISOLATE: RNA Target, Experiment 12, FIG. 2

( x i ) SEQUENCE DESCRIPTION: SEQ ID NO:18:

AUAAGGUAGA AGC                                                                                 13

( 2 ) INFORMATION FOR SEQ ID NO:19:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA Target, Experiment 13, FIG. 2

( x i ) SEQUENCE DESCRIPTION: SEQ ID NO:19:

ATAAGGAAGA AGC                                                                                 13

( 2 ) INFORMATION FOR SEQ ID NO:20:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( v i ) ORIGINAL SOURCE:
        ( C ) INDIVIDUAL ISOLATE: RNA Target, Experiment 14, FIG. 2

( x i ) SEQUENCE DESCRIPTION: SEQ ID NO:20:

AUAAGGAAGA AGC                                                                                 13

( 2 ) INFORMATION FOR SEQ ID NO:21:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO (iv) ANTI-SENSE: NO (vi) ORIGINAL SOURCE:
(C) INDIVIDUAL ISOLATE: RNA Target, Experiment 15, FIG. 2

(xi) SEQUENCE DESCRIPTION: SEQ ID NO:21:

AUAAGGUAGA AGC 13

(2) INFORMATION FOR SEQ ID NO:22:

(i) SEQUENCE CHARACTERISTICS:
(A) LENGTH: 26 base pairs
(B) TYPE: nucleic acid
(C) STRANDEDNESS: both
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: DNA Target Duplex, FIG. 8

(xi) SEQUENCE DESCRIPTION: SEQ ID NO:22:

TTCCTTCTTT CTTTTGAAAG AAGGAA 26

(2) INFORMATION FOR SEQ ID NO:23:

(i) SEQUENCE CHARACTERISTICS:
(A) LENGTH: 244 base pairs
(B) TYPE: nucleic acid
(C) STRANDEDNESS: both
(D) TOPOLOGY: linear (ii) MOLECULE TYPE: RNA (genomic)

(iii) HYPOTHETICAL: NO (vi) ORIGINAL SOURCE:
(C) INDIVIDUAL ISOLATE: HIV-1 REV RESPONSE ELEMENT (xi) SEQUENCE DESCRIPTION: SEQ ID NO:23:

CAGUGGGAAU AGGAGCUUUG UUCCUUGGGU UCUUGGGAGC AGCAGGAAGC ACUAUGGGCG 60

CAGCGUCAAU GACGCUGACG GUACAGGCCA GACAAUUAUU GUCUGGUAUA GUGCAGCAGC 120

AGAACAAUUU GCUGAGGGCU AUUGAGGCGC AACAGCAUCU GUUGCAACUC ACAGUCUGGG 180

GCAUCAAGCA GCUCCAGGCA AGAAUCCUGG CUGUGGAAAG AUACCUAAAG GAUCAACAGC 240

UCCU 244

(2) INFORMATION FOR SEQ ID NO:24:

(i) SEQUENCE CHARACTERISTICS:
(A) LENGTH: 69 base pairs
(B) TYPE: nucleic acid
(C) STRANDEDNESS: both
(D) TOPOLOGY: linear (ii) MOLECULE TYPE: RNA (genomic)

(iii) HYPOTHETICAL: NO (vi) ORIGINAL SOURCE:
(C) INDIVIDUAL ISOLATE: STEM II OF THE HIV-1 REV RESPONSE ELEMENT (xi) SEQUENCE DESCRIPTION: SEQ ID NO:24:

AGCACUAUGG GCGCAGCGUC AAUGACGCUG ACGGUACAGG CCAGACAAUU AUUGUCUGGU 60

AUAGUGCAG                                                                                                                                            69

( 2 ) INFORMATION FOR SEQ ID NO:25:

( i ) SEQUENCE CHARACTERISTICS:
        ( A ) LENGTH: 58 base pairs
        ( B ) TYPE: nucleic acid
        ( C ) STRANDEDNESS: both
        ( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
        ( C ) INDIVIDUAL ISOLATE: the sequence of the TAR site of
              HIV-1

( x i ) SEQUENCE DESCRIPTION: SEQ ID NO:25:

GGUCUCUCUG  GUUAGACCAG  AUCUGAGCCU  GGGAGCUCUC  UGGCUAACUA  GAGAACCC                    58

( 2 ) INFORMATION FOR SEQ ID NO:26:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 16-mer, phosphorothioate
              intersubunit linkages ( x i ) SEQUENCE DESCRIPTION: SEQ ID NO:26:

AAGGGCTTCT  TCCTTA                                                                      16

( 2 ) INFORMATION FOR SEQ ID NO:27:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 16-mer, phosphorothioate
              intersubunit linkages ( x i ) SEQUENCE DESCRIPTION: SEQ ID NO:27:

GAGTTCAAAA  GCCCTT                                                                      16